United States Patent
Zhang

(10) Patent No.: US 11,344,553 B2
(45) Date of Patent: May 31, 2022

(54) SUBSTITUTED PYRAZOLOPYRIMIDINES USEFUL AS KINASES INHIBITORS

(71) Applicant: TELIGENE LTD, Suzhou (CN)

(72) Inventor: Dawei Zhang, Thousand Oaks, CA (US)

(73) Assignee: Teligene Ltd., Suzhou (CN)

( * ) Notice: Subject to any disclaimer, the term of this patent is extended or adjusted under 35 U.S.C. 154(b) by 0 days.

(21) Appl. No.: 16/636,020

(22) PCT Filed: Aug. 9, 2018

(86) PCT No.: PCT/CN2018/099652
§ 371 (c)(1),
(2) Date: Feb. 2, 2020

(87) PCT Pub. No.: WO2010/048314
PCT Pub. Date: Apr. 29, 2010

(65) Prior Publication Data
US 2021/0315899 A1    Oct. 14, 2021

Related U.S. Application Data

(60) Provisional application No. 62/605,390, filed on Aug. 11, 2017.

(51) Int. Cl.
| | | |
|---|---|---|
| A61K 31/519 | (2006.01) | |
| A61K 45/06 | (2006.01) | |
| C07D 487/04 | (2006.01) | |
| A61P 35/00 | (2006.01) | |

(52) U.S. Cl.
CPC ............ *A61K 31/519* (2013.01); *A61K 45/06* (2013.01); *C07D 487/04* (2013.01); *A61P 35/00* (2018.01)

(58) Field of Classification Search
CPC .... C07D 487/04; A61K 31/519; A61K 45/06; A61P 35/00
See application file for complete search history.

(56) References Cited

FOREIGN PATENT DOCUMENTS

| | | | |
|---|---|---|---|
| WO | 2010048314 A1 | 10/2009 | |
| WO | WO-2010048314 A1 * | 4/2010 | ............. A61K 45/06 |

OTHER PUBLICATIONS

Mandal, "How to Prevent Cancer", http://news-medical.net/health/How-to-Prevent-Cancer.aspx, pp. 1-4, publ. online Aug. 29, 2013 (Year: 2013).*
Rodriguez, "Know the Most Common Types of Cancer", Everyday Health, publ. online Feb. 8, 2010, pp. 1-13 (Year: 2010).*
Wistuba et al., Nature Rev., Clin. Oncology, publ 2011, vol. 8, pp. 135-141 (Year: 2011).*
Bhatia et al., Nature Biotechnology, publ 2012, vol. 30(7), pp. 604-610 (Year: 2012).*
Kaiser, Science, publ 2012, vol. 337, pp. 282-284 (Year: 2012).*

* cited by examiner

*Primary Examiner* — Sarah Pihonak
(74) *Attorney, Agent, or Firm* — Feng Tian

(57) ABSTRACT

The present disclosure is directed to novel pyrzaolopyrimidines, their derivatives, pharmaceutically acceptable salts, solvates and hydrates thereof. The compounds and compositions of the present disclosure have protein kinases inhibitory activities and are expected to be useful for the treatment of protein kinases mediated diseases and conditions.

18 Claims, No Drawings
Specification includes a Sequence Listing.

SUBSTITUTED PYRAZOLOPYRIMIDINES USEFUL AS KINASES INHIBITORS

CROSS REFERENCE

This application claims the benefit of U.S. Provisional Patent Application No. 62/605,390, filed on Aug. 11, 2017, which is incorporated herein by reference in its entirety.

TECHNICAL FIELD

The disclosure is directed to kinase inhibitors. This disclosure also relates to pharmaceutical compositions comprising kinases inhibitors and to the use of kinases inhibitors and pharmaceutical compositions comprising kinases inhibitors to treat disease such as cancers.

SEQUENCE LISTING

The instant application contains a Sequence Listing which has been submitted in ASCII format via EFS-Web and is hereby incorporated by reference in its entirety. Said ASCII copy, created on Apr. 8, 2021, is named 62000.022_SL.txt and is 702 bytes in size.

BACKGROUND

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. For example, protein tyrosine kinases (PTKs) are enzymes, which catalyze the phosphorylation of specific tyrosine residues in cellular proteins. Examples of kinases in the protein kinase family include, without limitation, Abl1 (v-Abl Abelson murine leukemia viral oncogene homolog 1), Akt, Alk, Bcr-Abl1, Blk, Brk, Btk, c-Kit, c-Met, c-Src, c-Fms, CDK1-10, b-Raf, c-Raf1, CSF1R, CSK, EGFR, ErbB2, ErbB3, ErbB4, Erk, FGFR1, FGFR2, FGFR3, FGFR4, FGFR5, Flt-1, Fps, Frk, Jak, KDR, MEK, PDGFR, PIK, PKC, PYK2, Ros, Tie, Tie2, and Zap70. Due to their activity in numerous cellular processes, protein kinases have emerged as important therapeutic targets.

The association between overexpression, activation, amplification and/or mutation of Trks and several cancers as seen with studies conduct on neuroblastoma (Brodeur, G. M., *Nat. Rev. Cancer* 2003, 3, 203-216), ovarian cancer (Kruettgen et al., *Brain Pathology* 2006, 16: 304-310), prostate cancer (Dionne et al., Clin. Cancer Res. 1998, 4(8): 1887-1898), pancreatic cancer (Dang et al., *J. Gastroenterol. Hepatol.* 2006, 21(5): 850-858), large cell neuroendocrine tumors (Marchetti et al., *Human Mutation* 2008,29(5),609-616, and colorectal cancer (Bardelli, A., *Science* 2003, 300, 949) support the reasoning that therapeutic implications of an effective Trk inhibitor may extend far beyond pain therapy. See also W007013673, W007025540, W008052734, W020121158413 and US Patent Application U.S. Ser. No. 61/650,019.

SUMMARY

In one aspect of the present disclosure, there are provided compounds of Formula I:

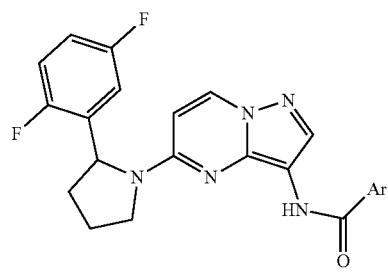

I or a pharmaceutically acceptable salt, solvate, prodrug, stereoisomer, tautomer or metabolite thereof, wherein Ar is substituted $C_6$-$C_{12}$ aryl or substituted $C_5$-$C_{12}$ heteroaryl, the proviso that Ar is the following residue when Ar is substituted $C_5$-$C_{12}$ heteroaryl:

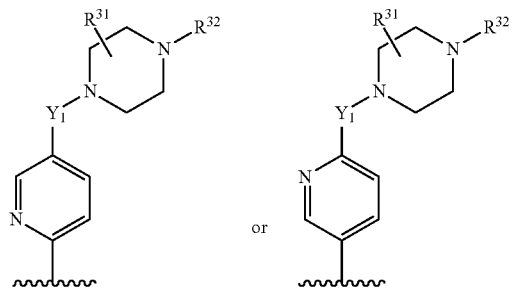

wherein $Y_1$ is a bond or $CR^{23}R^{24}$;

$R^{31}$ is one or more groups independently selected from the group consisting of hydrogen, $C_1$-$C_3$ alkyl and deuterium;

$R^{32}$ is $C_1$-$C_3$ alkyl, $CO(C_1$-$C_3$ alkyl) or hydrogen;

each of $R^{23}$ and $R^{24}$ is independently hydrogen, deuterium, or $C_1$-$C_3$ alkyl.

In another aspect of the present disclosure, there are provided compounds of Formula II:

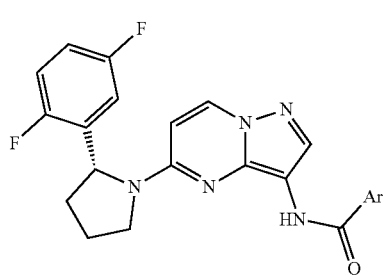

II or a pharmaceutically acceptable salt, solvate, prodrug, stereoisomer, tautomer or metabolite thereof, wherein Ar is substituted $C_6$-$C_{12}$ aryl or substituted $C_5$-$C_{12}$ heteroaryl, the proviso that Ar is the following residue when Ar is substituted $C_5$-$C_{12}$ heteroaryl:

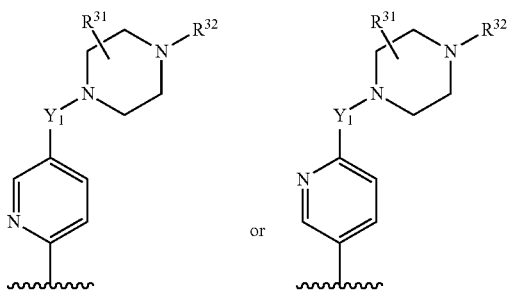
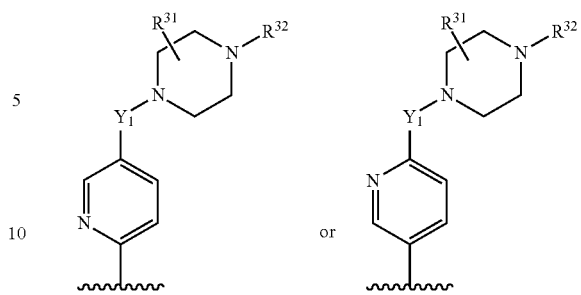

wherein $Y_1$ is a bond or $CR^{23}R^{24}$;

$R^{31}$ is one or more groups independently selected from the group consisting of hydrogen, $C_1$-$C_3$ alkyl and deuterium;

$R^{32}$ is $C_1$-$C_3$ alkyl, $CO(C_1$-$C_3$ alkyl) or hydrogen;

each of $R^{23}$ and $R^{24}$ is independently hydrogen, deuterium, or $C_1$-$C_3$ alkyl.

In another aspect of the present disclosure, there are provided pharmaceutical compositions comprising a compound of the present disclosure and a pharmaceutically acceptable carrier.

In still another aspect of the present disclosure, there are provided methods of treating or preventing a hyper-proliferative disorder in a patient, comprising the step of administering to the patient in need thereof a pharmaceutical composition described above.

In another aspect of the present disclosure, there are provided compounds of the present disclosure for use as a medicament.

In still another aspect of the present disclosure, there is provided a compound of the present disclosure for use as a medicament for treating or preventing various cancers.

In still another aspect of the present disclosure, there is provided a compound of the present disclosure for use in a method of regulating the kinase signaling transduction.

In still another aspect of the present disclosure, there is provided a compound of the present disclosure in combination with one more anti-cancer agents for use in a method of treating or preventing a hyper-proliferative disorder.

DETAILED DESCRIPTION

In one aspect of the present disclosure, there are provided compounds of Formula I:

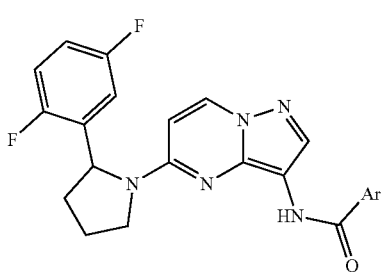

I or a pharmaceutically acceptable salt, solvate, prodrug, stereoisomer, tautomer or metabolite thereof, wherein Ar is substituted $C_6$-$C_{12}$ aryl or substituted $C_5$-$C_{12}$ heteroaryl, the proviso that Ar is the following residue when Ar is substituted $C_5$-$C_{12}$ heteroaryl:

wherein $Y_1$ is a bond or $CR^{23}R^{24}$;

$R^{31}$ is one or more groups independently selected from the group consisting of hydrogen, $C_1$-$C_3$ alkyl and deuterium;

$R^{32}$ is $C_1$-$C_3$ alkyl, $CO(C_1$-$C_3$ alkyl) or hydrogen;

each of $R^{23}$ and $R^{24}$ is independently hydrogen, deuterium, or $C_1$-$C_3$ alkyl.

In some embodiments of the present disclosure, there are provided compounds of Formula II:

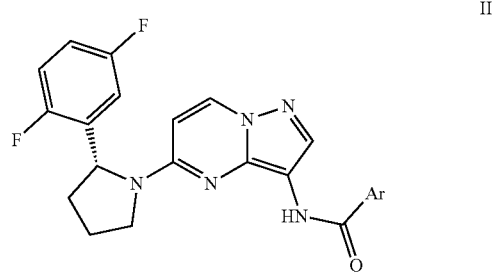

II or a pharmaceutically acceptable salt, solvate or a prodrug or a stereoisomer or a tautomer or metabolite thereof, wherein Ar is substituted $C_6$-$C_{12}$ aryl or substituted $C_5$-$C_{12}$ heteroaryl, the proviso that Ar is the following residue when Ar is substituted $C_5$-$C_{12}$ heteroaryl:

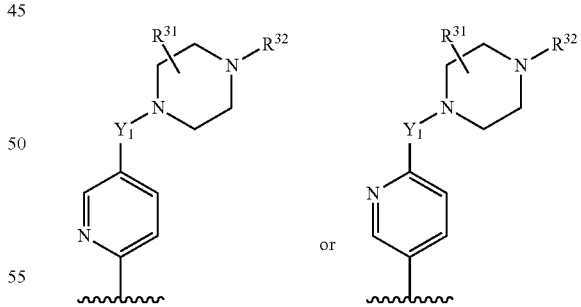

wherein $Y_1$ is a bond or $CR^{23}R^{24}$;

$R^{31}$ is one or more groups independently selected from the group consisting of hydrogen, $C_1$-$C_3$ alkyl and deuterium;

$R^{32}$ is $C_1$-$C_3$ alkyl, $CO(C_1$-$C_3$ alkyl) or hydrogen;

each of $R^{23}$ and $R^{24}$ is independently hydrogen, deuterium, or $C_1$-$C_3$ alkyl.

In some embodiments of the present disclosure, there are provided compounds according to Formula I:

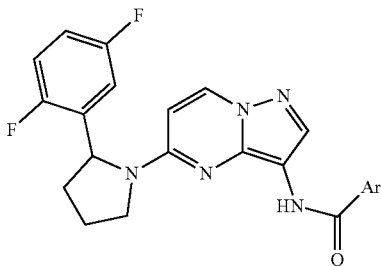

I

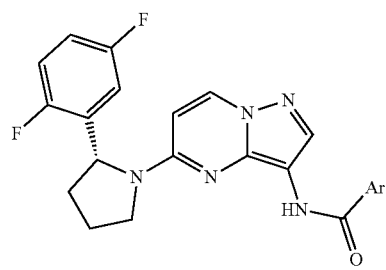

II or a pharmaceutically acceptable salt, solvate, prodrug, stereoisomer, tautomer or metabolite thereof, wherein
Ar is

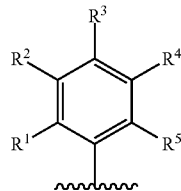

wherein at least one of $R^1$, $R^2$, $R^3$, $R^4$, and $R^5$ is not hydrogen, $R^1$, $R^2$, $R^3$, $R^4$, and $R^5$ are independently hydrogen, halide, $C_1$-$C_6$ alkyl, $C_1$-$C_6$ alkyloxy, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, —$NR^6R^7$, —$CR^8R^9(CR^8R^9)_nOR^6$, CN, —$C(O)R^6$, —$O(CO)R^6$, —$OCR^8R^9(CR^8R^9)_nNR^6R^7$, —$OCR^8R^9(CR^8R^9)_nOR^6$, —$NR^6C(O)R^7$, —$(CR^8R^9)_nC(O)OR^6$, —$(CR^8R^9)_nC(O)NR^6R^7$, —$CR^8R^9(CR^8R^9)_nNR^6R^7$, —$NR^6(CO)$—$NR^6R^7$, —$NR^6S(O)_pR^7$, —$S(O)_tR^6$, or —$S(O)_2NR^6R^7$, wherein two groups among $R^1$, $R^2$, $R^3$, $R^4$, and $R^5$ on adjacent atoms of the phenyl may, together with the adjacent atoms to which two groups are bound, be combined to form a $C_6$-$C_{12}$ aryl, 5-12 membered heteroaryl, $C_3$-$C_{12}$ cycloalkyl or 3-12 membered heteroalicyclic, wherein each aryl, heteroalicyclic, and heteroaryl is unsubstituted or independently substituted with one or more deuterium or $C_1$-$C_3$ alkyl; with the proviso that the heteroatom of 3-12 membered heteroalicyclic is not attached to the phenyl;

each $R^6$, $R^7$, $R^8$, and $R^9$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^6$, $R^7$, $R^8$, and $R^9$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^6$, $R^7$, $R^8$, and $R^9$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;

each n is independently 0, 1, 2, 3, or 4;

each p is independently 1 or 2; and each t is independently 0, 1, or 2.

In some embodiments of the present disclosure, there are provided compounds of Formula II:

or a pharmaceutically acceptable salt, solvate or a prodrug or a stereoisomer or a tautomer or metabolite thereof, wherein
Ar is the substituted phenyl, i.e. the following residue:

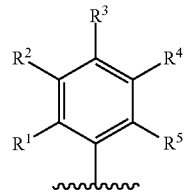

wherein at least one of $R^1$, $R^2$, $R^3$, $R^4$, and $R^5$ is not hydrogen, $R^1$, $R^2$, $R^3$, $R^4$, and $R^5$ are independently hydrogen, halide, $C_1$-$C_6$ alkyl, $C_1$-$C_6$ alkyloxy, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, —$NR^6R^7$, —$CR^8R^9(CR^8R^9)_nOR^6$, CN, —$C(O)R^6$, —$O(CO)R^6$, —$OCR^8R^9(CR^8R^9)_nNR^6R^7$, —$OCR^8R^9(CR^8R^9)_nOR^6$, —$NR^6C(O)R^7$, —$(CR^8R^9)_nC(O)OR^6$, —$(CR^8R^9)_nC(O)NR^6R^7$, —$CR^8R^9(CR^8R^9)_nNR^6R^7$, —$NR^6(CO)$—$NR^6R^7$, —$NR^6S(O)_pR^7$, —$S(O)_tR^6$, or —$S(O)_2NR^6R^7$, wherein two groups among $R^1$, $R^2$, $R^3$, $R^4$, and $R^5$ on adjacent atoms of the phenyl may, together with the adjacent atoms to which two groups are bound, be combined to form a $C_6$-$C_{12}$ aryl, 5-12 membered heteroaryl, $C_3$-$C_{12}$ cycloalkyl or 3-12 membered heteroalicyclic, wherein each aryl, heteroalicyclic, and heteroaryl is unsubstituted or independently substituted with one or more deuterium or $C_1$-$C_3$ alkyl; with the proviso that the heteroatom of 3-12 membered heteroalicyclic is not attached to the phenyl;

each $R^6$, $R^7$, $R^8$, and $R^9$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^6$, $R^7$, $R^8$, and $R^9$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^6$, $R^7$, $R^8$, and $R^9$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;

each n is independently 0, 1, 2, 3, or 4;

each p is independently 1 or 2; and each t is independently 0, 1, or 2.

In some embodiments of the present disclosure, there are provided compounds of Formula I or Formula II, wherein Ar is the substituted phenyl, i.e. the following residue:

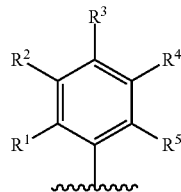

wherein at least one of $R^1$, $R^2$, $R^3$, $R^4$, and $R^5$ is not hydrogen, $R^1$, $R^2$, $R^3$, $R^4$, and $R^5$ are independently hydrogen, halide, $C_1$-$C_6$ alkyl, $C_1$-$C_6$ alkyloxy, $C_2$-$C_6$ alkenyl, $C_2$-$C_6$ alkynyl, $C_3$-$C_6$ cycloalkyl, $C_6$-$C_{12}$ aryl, 3-12 membered heteroalicyclic, 5-12 membered heteroaryl, $NO_2$, —$NR^6R^7$, —$CR^8R^9(CR^8R^9)_nOR^6$, CN, —$C(O)R^6$, —$O(CO)R^6$, —$OCR^8R^9(CR^8R^9)_nNR^6R^7$, —$OCR^8R^9$ $(CR^8R^9)_nOR^6$, —$NR^6C(O)R^7$, —$(CR^8R^9)_nC(O)OR^6$, —$(CR^8R^9)_nC(O)NR^6R^7$, —$CR^8R^9(CR^8R^9)_nNR^6R^7$, —$NR^6(CO)$—$NR^6R^7$, —$NR^6S(O)_pR^7$, —$S(O)_rR^6$, or —$S(O)_2NR^6R^7$, wherein two groups among $R^1$, $R^2$, $R^3$, $R^4$, and $R^5$ on adjacent atoms of the phenyl may, together with the adjacent atoms to which two groups are bound, be combined to form a $C_6$-$C_{12}$ aryl, 5-12 membered heteroaryl, $C_3$-$C_{12}$ cycloalkyl or 3-12 membered heteroalicyclic, wherein each aryl, heteroalicyclic, and heteroaryl is unsubstituted or independently substituted with one or more deuterium or $C_1$-$C_3$ alkyl.

In some embodiments of the present disclosure, there are provided compounds of Formula I, wherein Ar is the following residue:

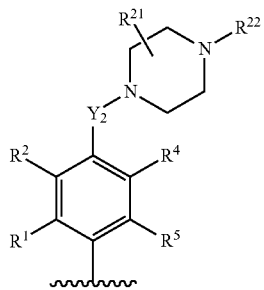

wherein $Y_2$ is a bond or $CR^{23}R^{24}$;
$R^1$, $R^2$, $R^4$, and $R^5$ are independently hydrogen, halide, $CF_3$, $C_1$-$C_3$ alkyl, $NO_2$, $C_1$-$C_3$ alkoxyl, or oxan-4-ylamino;
$R^{21}$ is one or more groups independently selected from the group consisting of hydrogen, $C_1$-$C_3$ alkyl and deuterium;
$R^{22}$ is $C_1$-$C_3$ alkyl, $CO(C_1$-$C_3$ alkyl) or hydrogen;
each of $R^{23}$ and $R^{24}$ is independently hydrogen, deuterium, or $C_1$-$C_3$ alkyl.

In some embodiments of the present disclosure, there are provided compounds of Formula II, wherein Ar is the following residue:

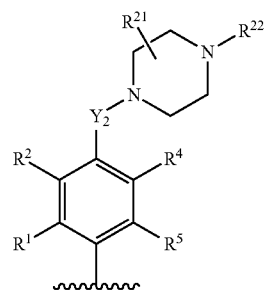

wherein $Y_2$ is a bond or $CR^{23}R^{24}$;
$R^1$, $R^2$, $R^4$, and $R^5$ are independently hydrogen, halide, $CF_3$, $C_1$-$C_3$ alkyl, $NO_2$, $C_1$-$C_3$ alkoxyl, or oxan-4-ylamino;
$R^{21}$ is one or more groups independently selected from the group consisting of hydrogen, $C_1$-$C_3$ alkyl and deuterium;
$R^{22}$ is $C_1$-$C_3$ alkyl, $CO(C_1$-$C_3$ alkyl) or hydrogen;
each of $R^{23}$ and $R^{24}$ is independently hydrogen, deuterium, or $C_1$-$C_3$ alkyl.

In some embodiments of the present disclosure, there are provided compounds of Formula I, wherein Ar is the following residue:

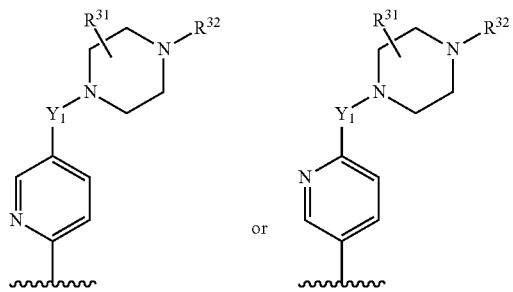

wherein $Y_1$ is a bond or $CR^{23}R^{24}$;
$R^{31}$ is one or more groups independently selected from the group consisting of hydrogen, $C_1$-$C_3$ alkyl and deuterium;
$R^{32}$ is $C_1$-$C_3$ alkyl, $CO(C_1$-$C_3$ alkyl) or hydrogen;
each of $R^{23}$ and $R^{24}$ is independently hydrogen, deuterium, or $C_1$-$C_3$ alkyl.

In some embodiments of the present disclosure, there are provided compounds of Formula I, wherein Ar is the following residue:

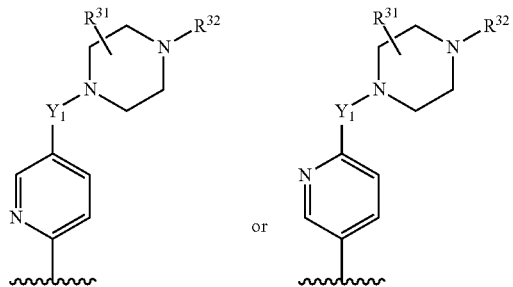

wherein $Y_1$ is a bond or $CR^{23}R^{24}$;
$R^{31}$ is one or more groups independently selected from the group consisting of hydrogen, $C_1$-$C_3$ alkyl and deuterium;
$R^{32}$ is $C_1$-$C_3$ alkyl, $CO(C_1$-$C_3$ alkyl) or hydrogen;
each of $R^{23}$ and $R^{24}$ is independently hydrogen, deuterium, or $C_1$-$C_3$ alkyl.

In some embodiments of the present disclosure, there are provided compounds selected from the group consisting of:
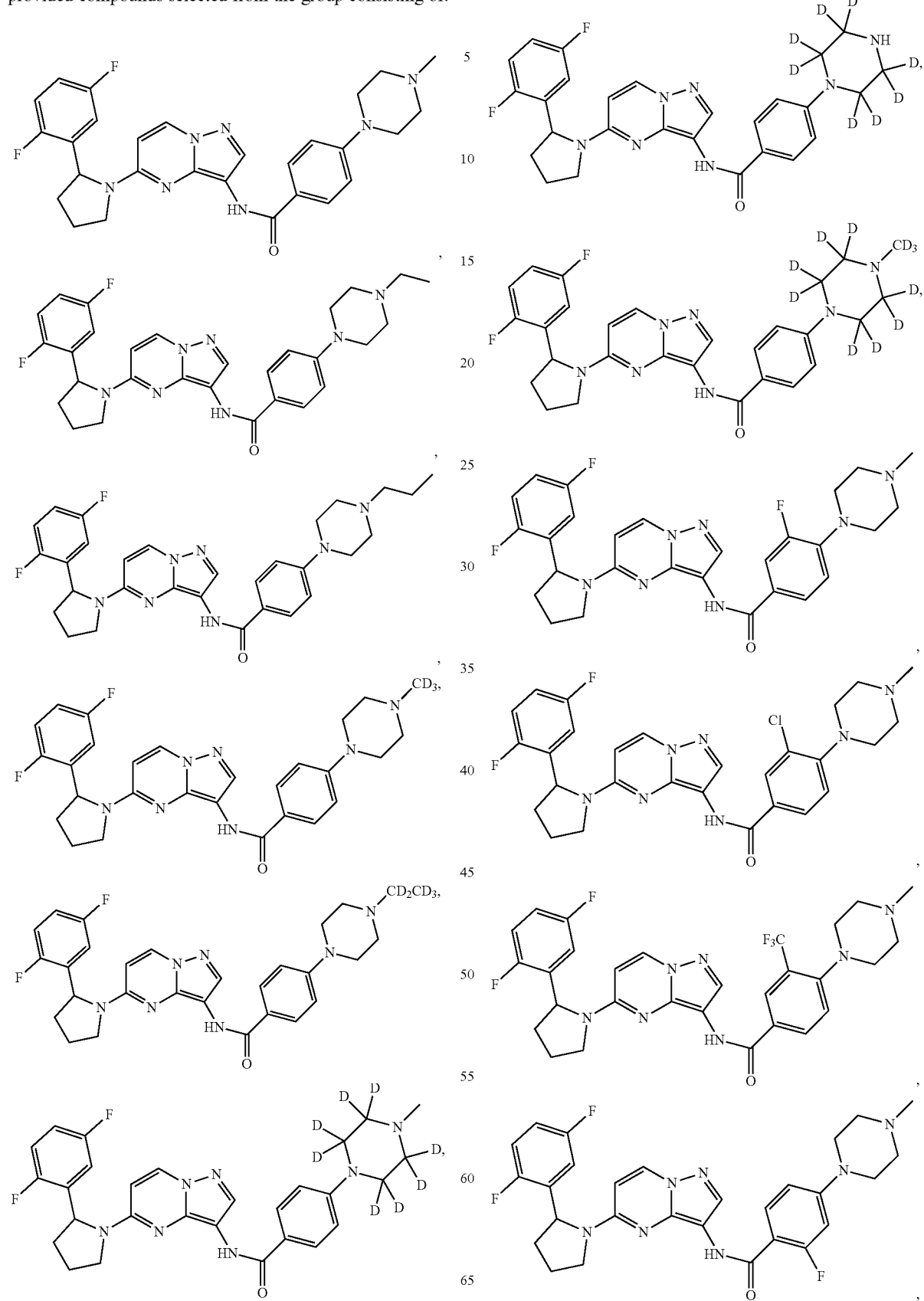

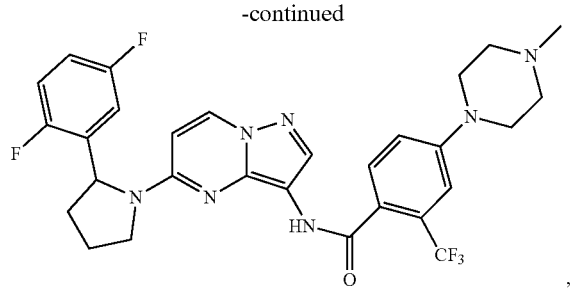,
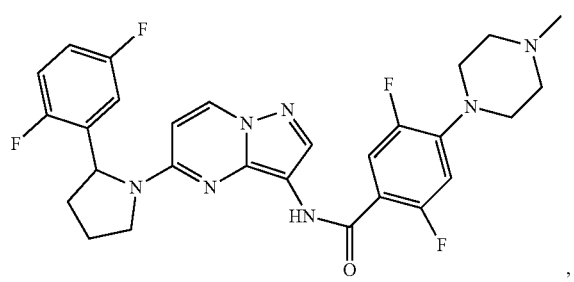,
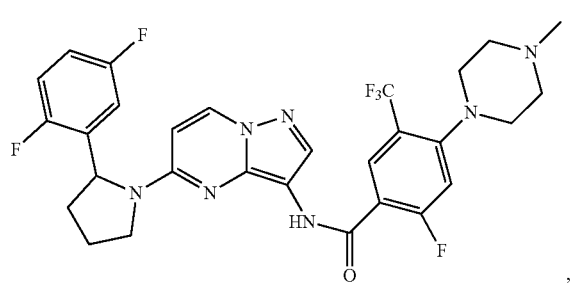,
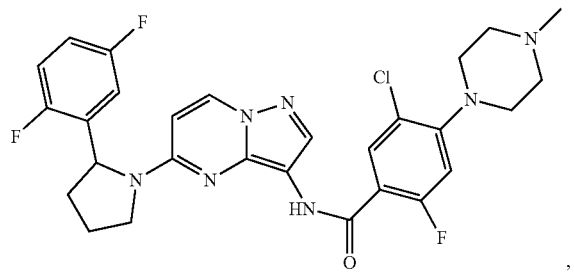,
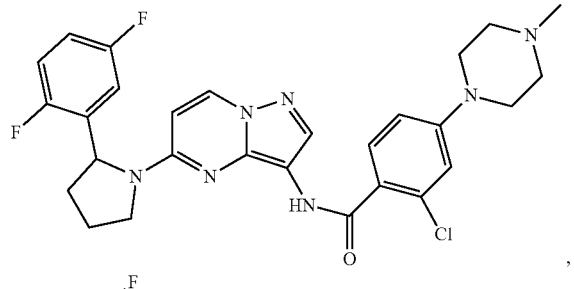,
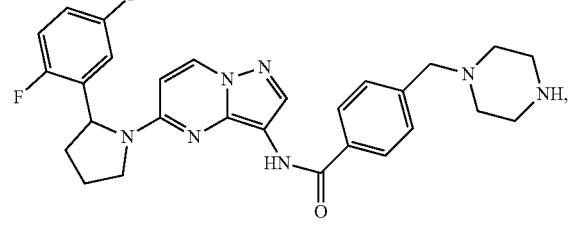,
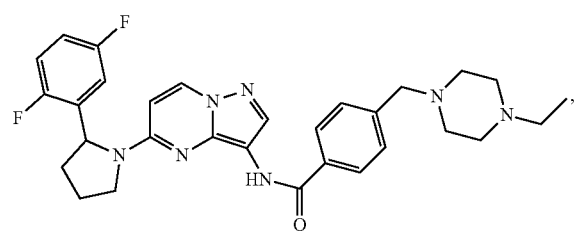,
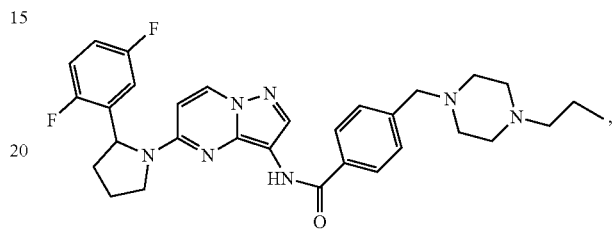,
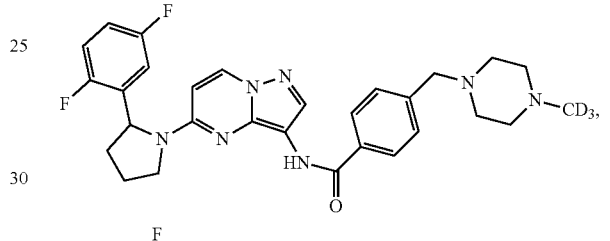,
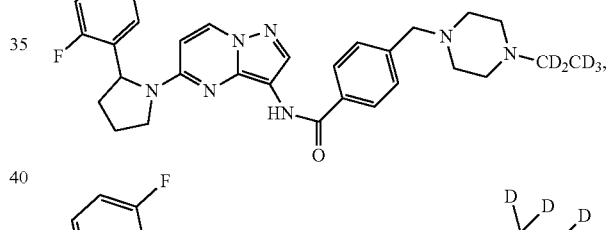,
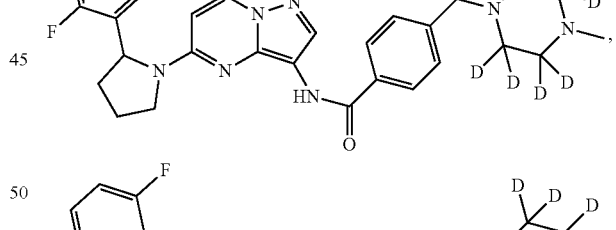,
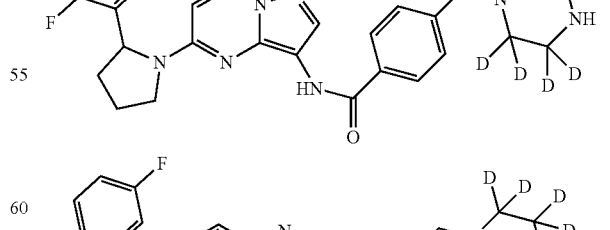,

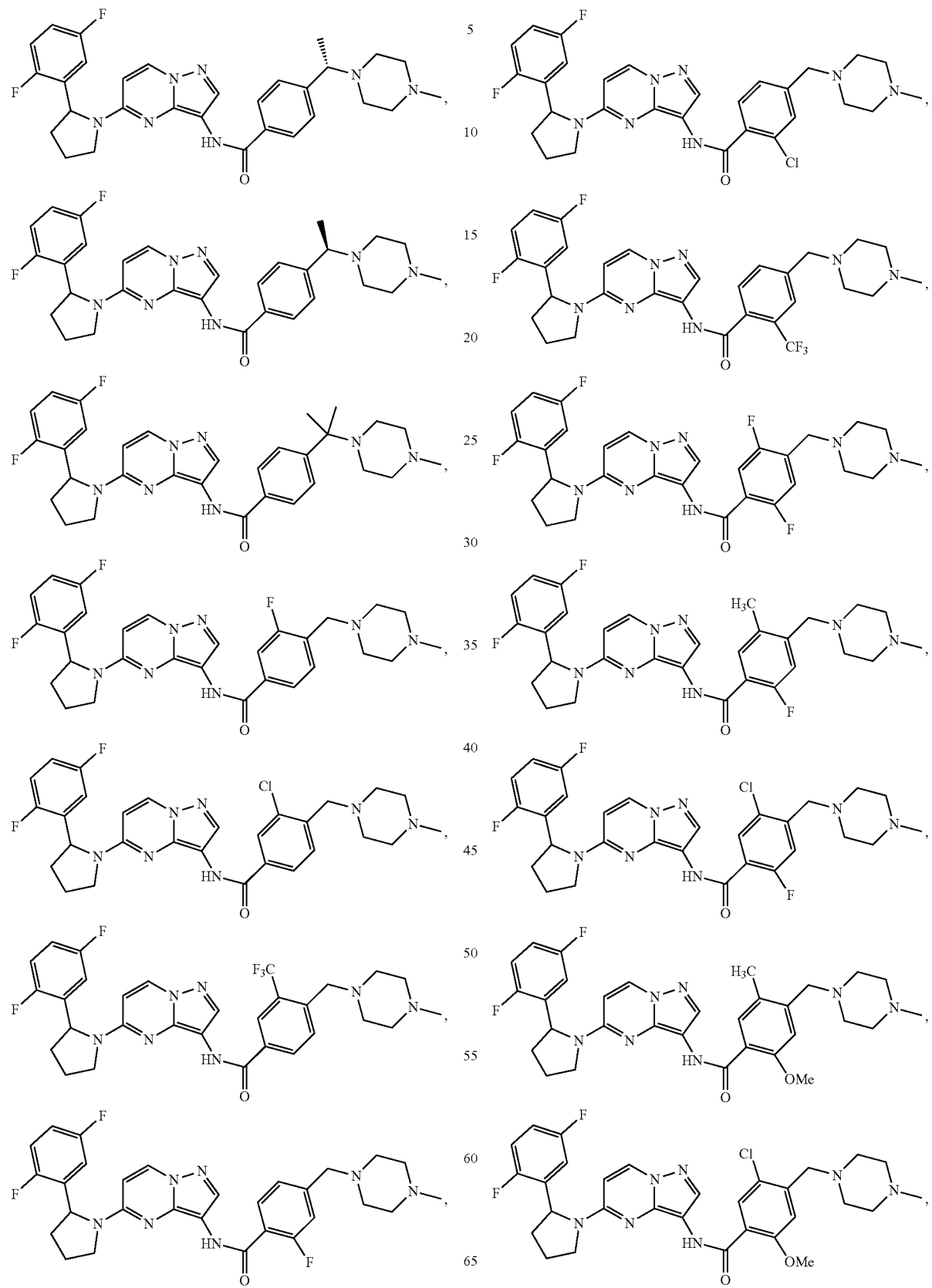

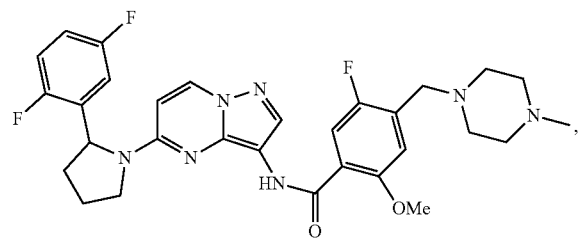
,
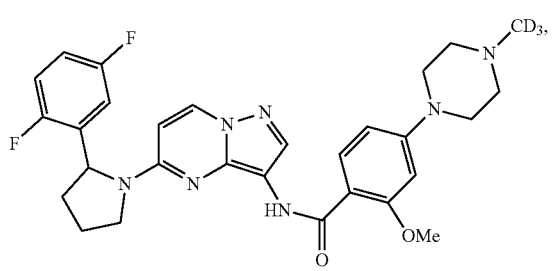
,
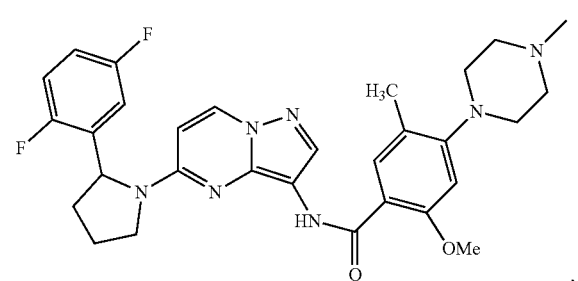
,
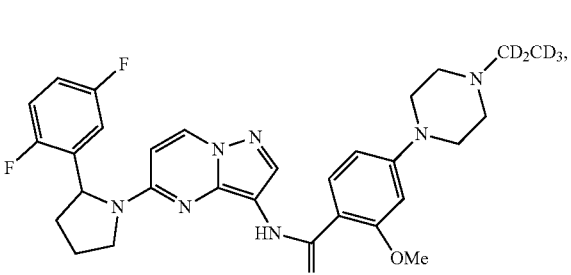
,
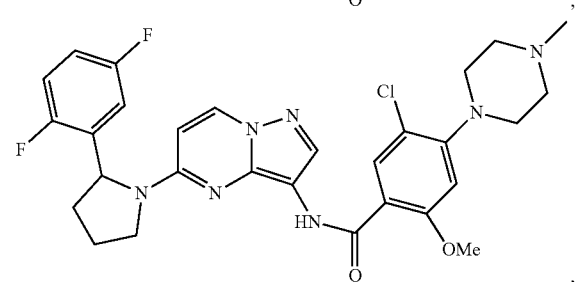
,
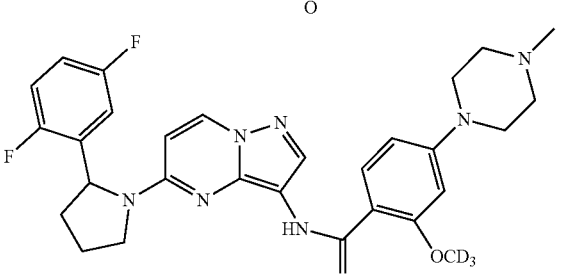
,
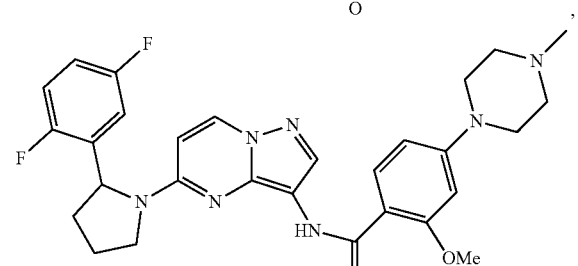
,
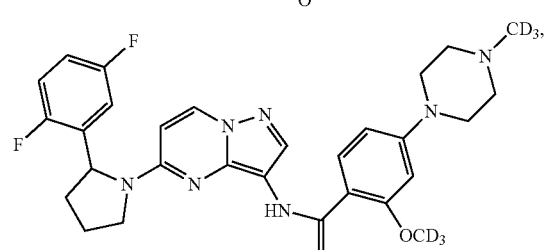
,

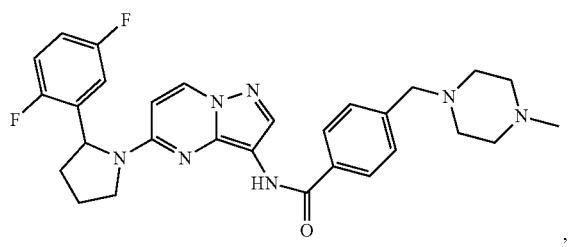
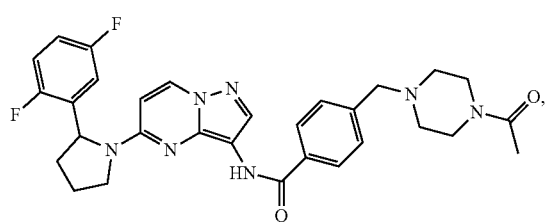
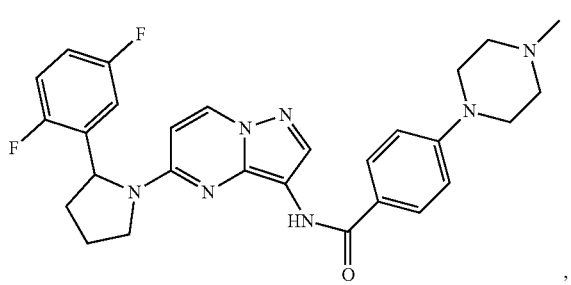 [SMILES: COc1cc(N2CCN(C)CC2)ccc1C(=O)Nc1cnn2ccc(N3CCC[C@@H]3c3cc(F)ccc3F)nc12]
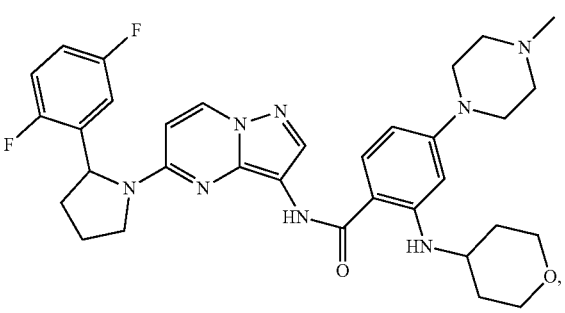
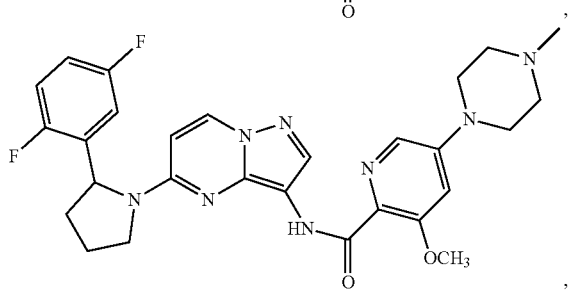
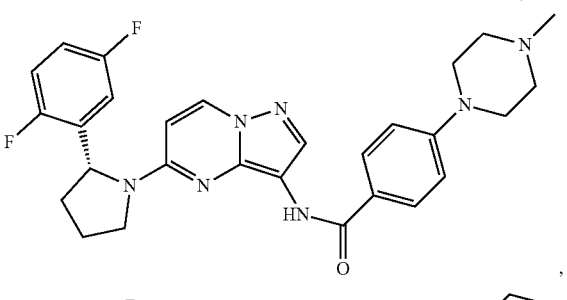
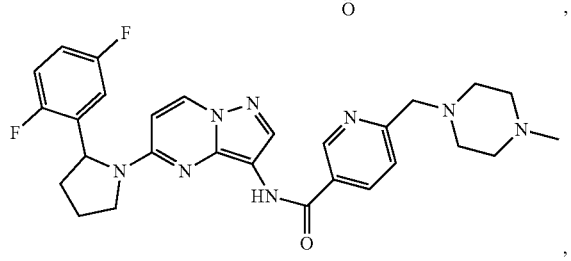
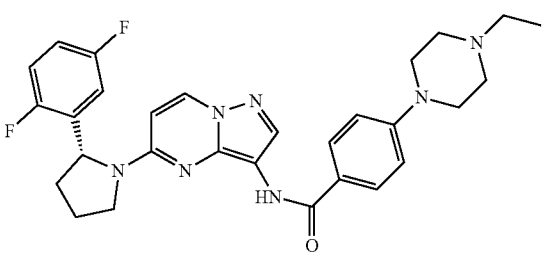
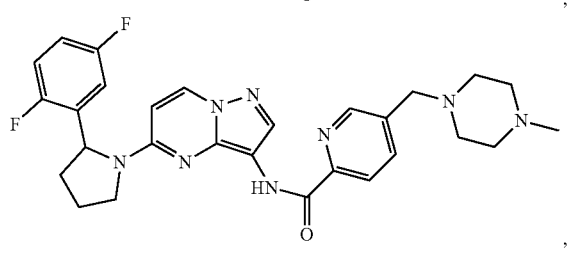
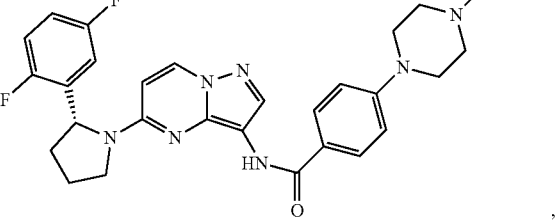
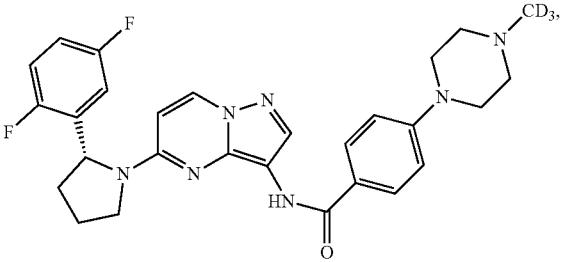

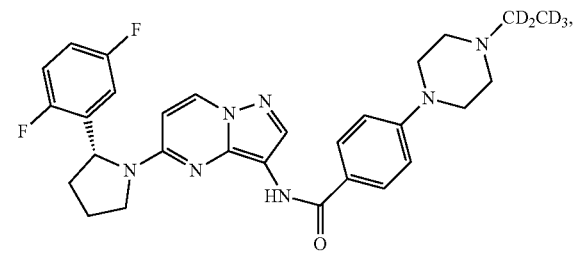
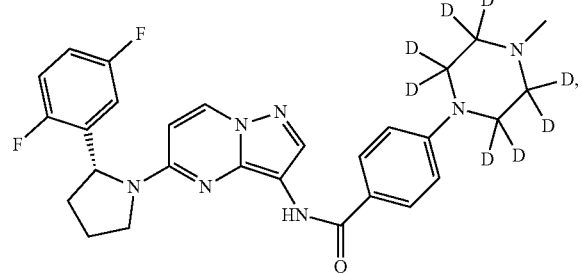
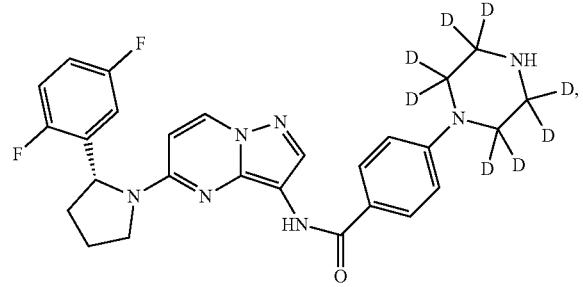
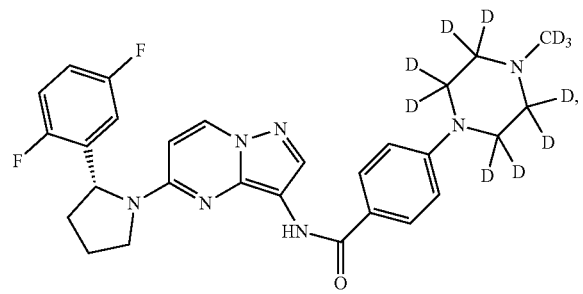
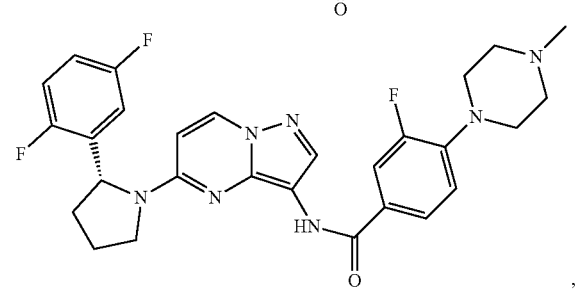
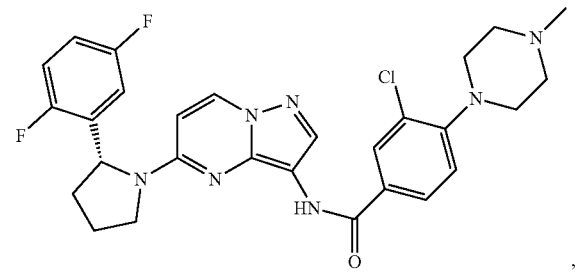
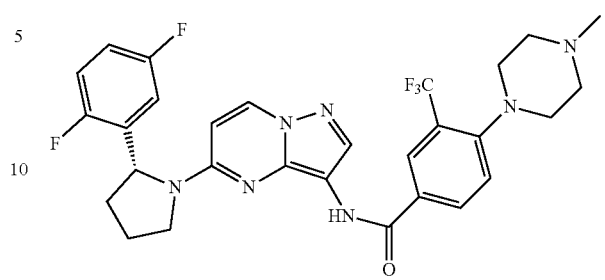
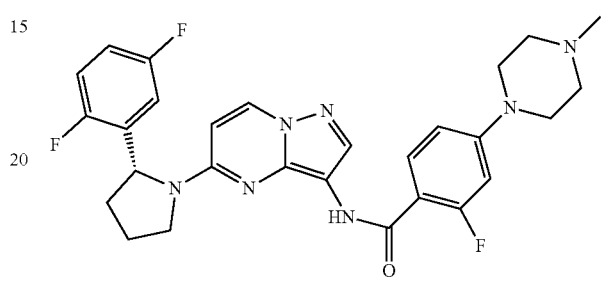
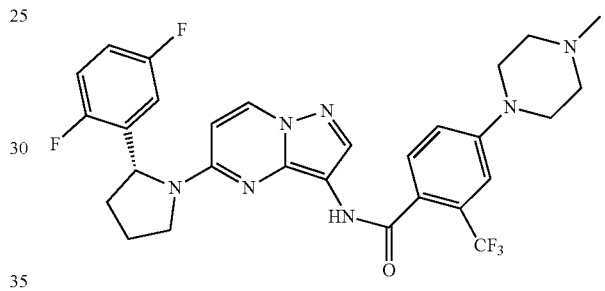
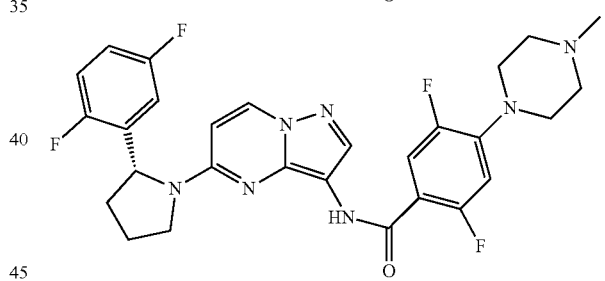
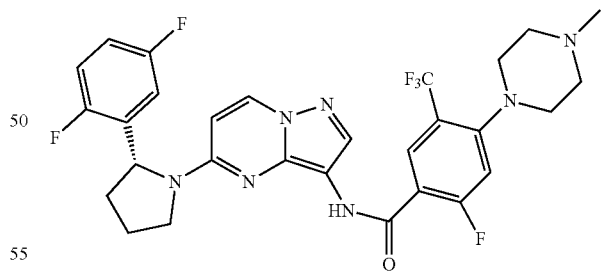
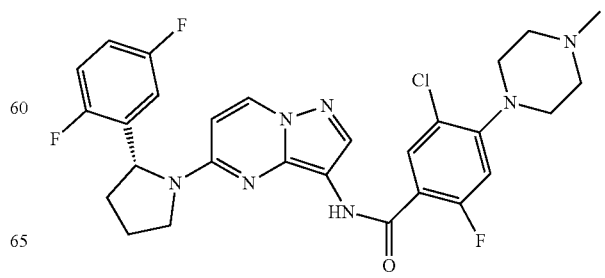

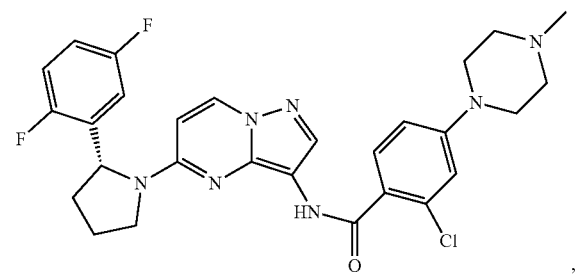
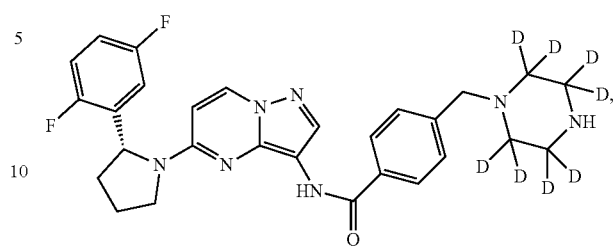
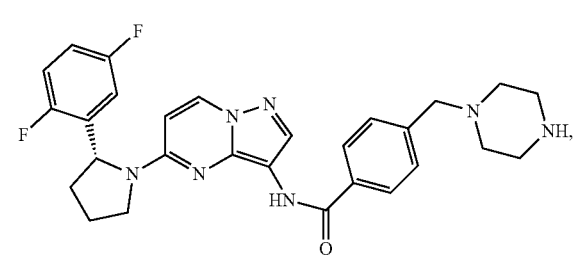
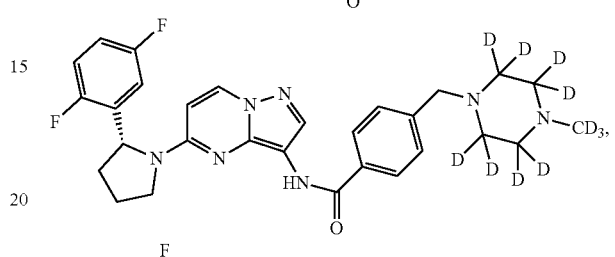
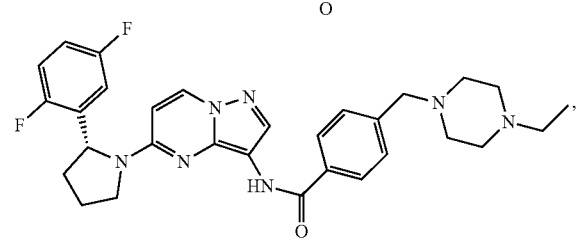
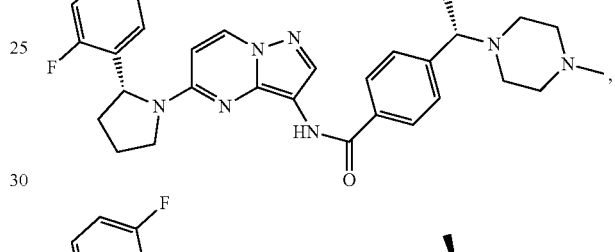
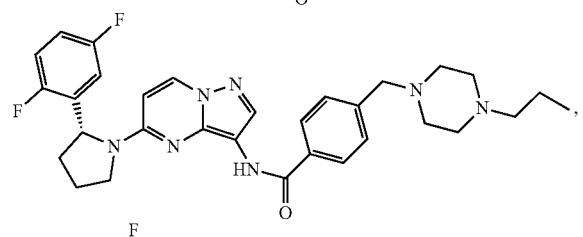
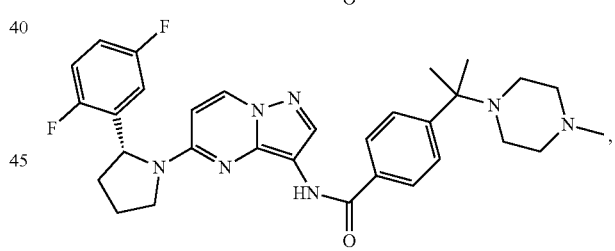
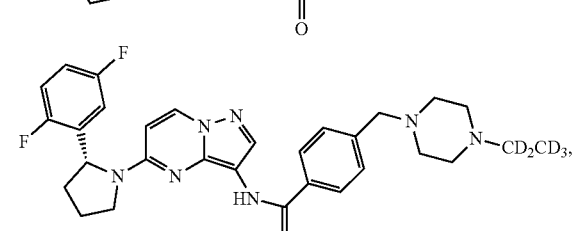
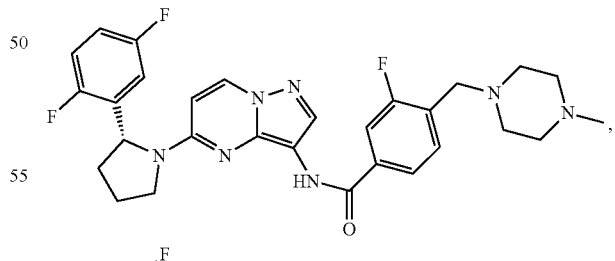
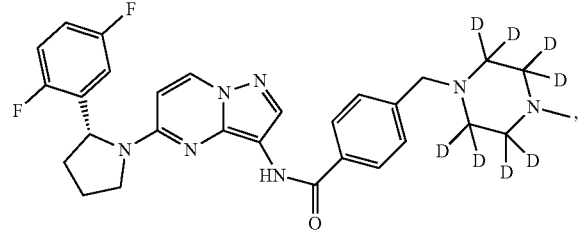
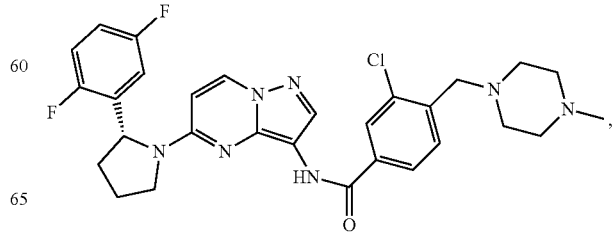

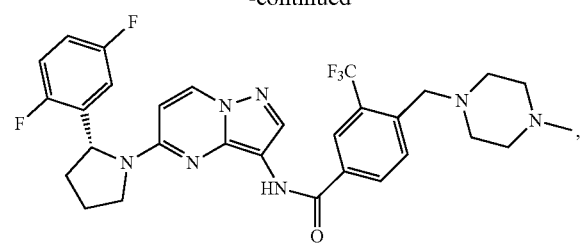
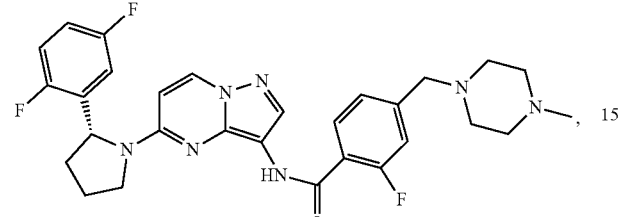
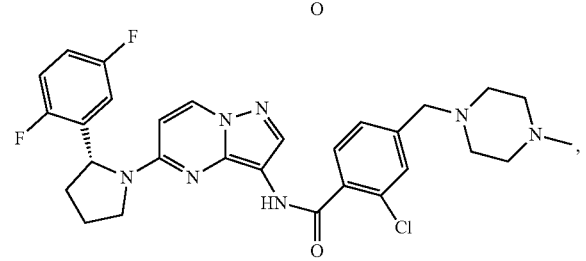
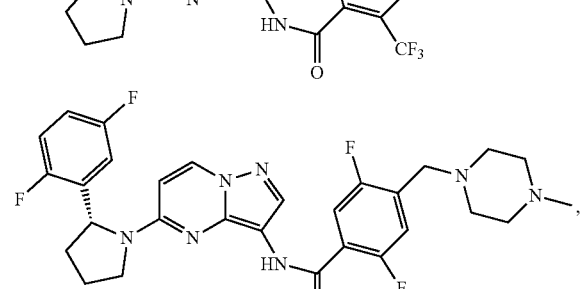
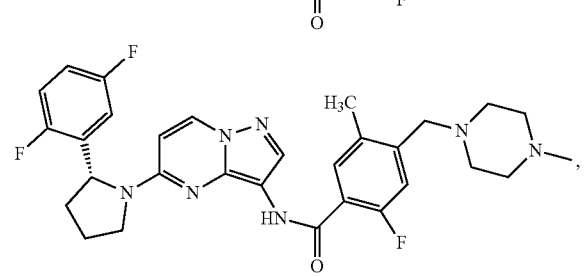
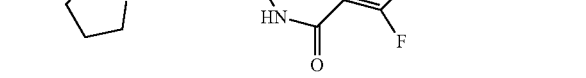
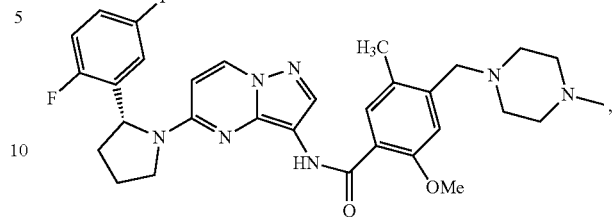
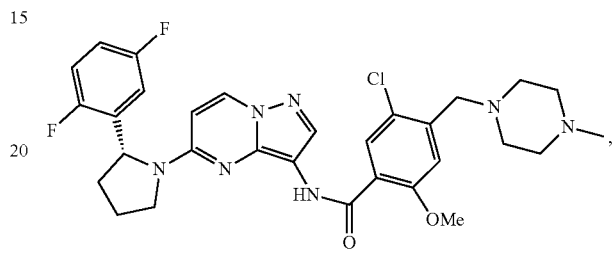
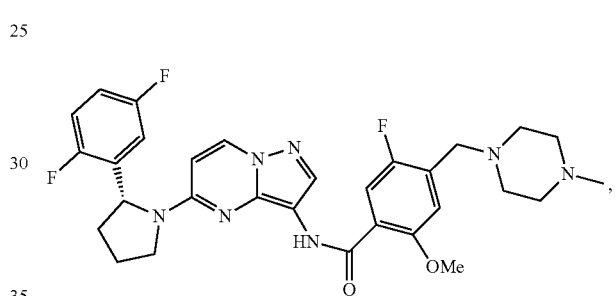
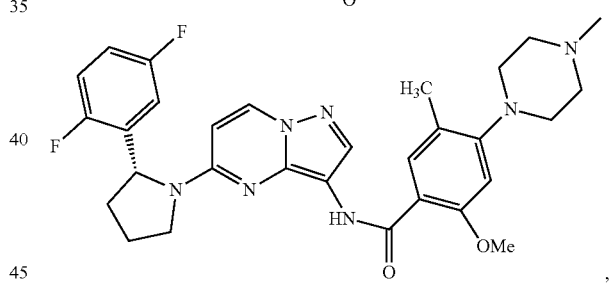
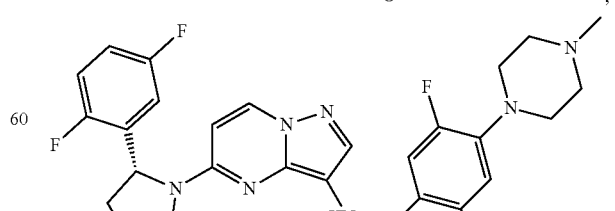
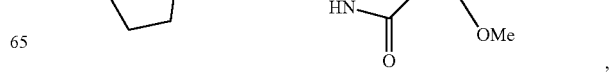

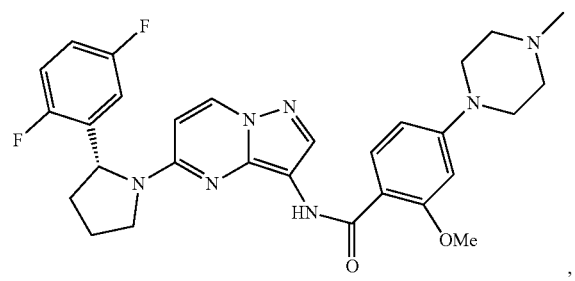,
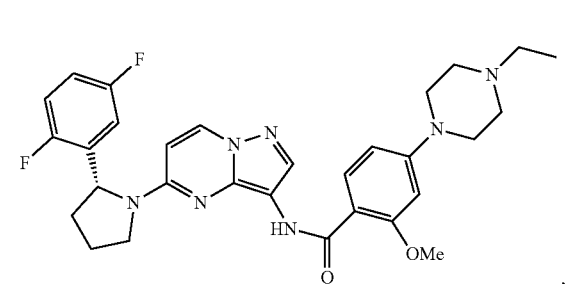,
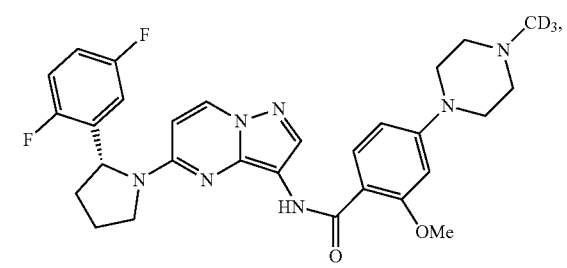,
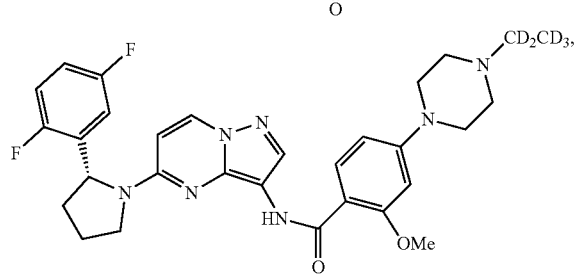,
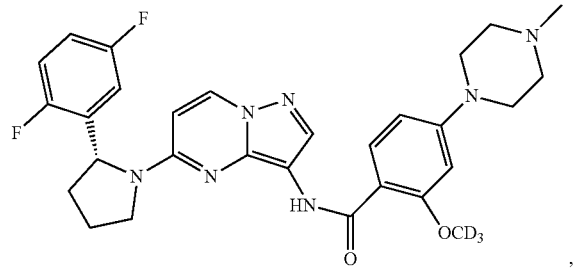,
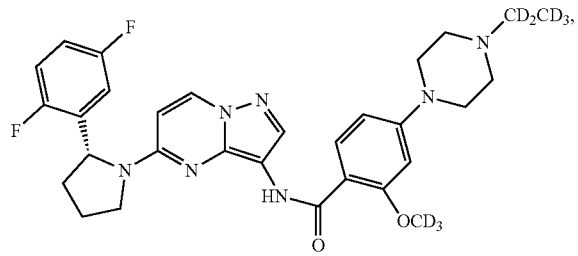,
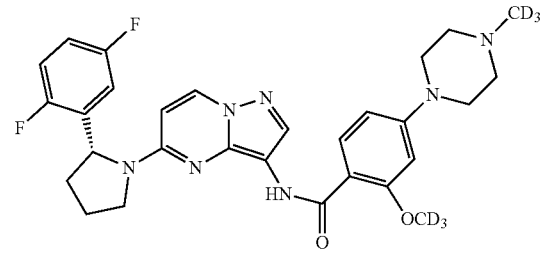,
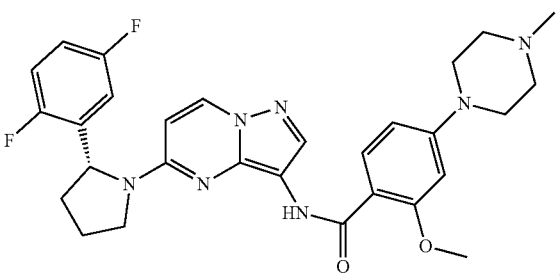,
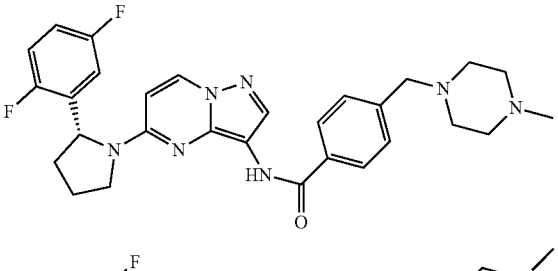,
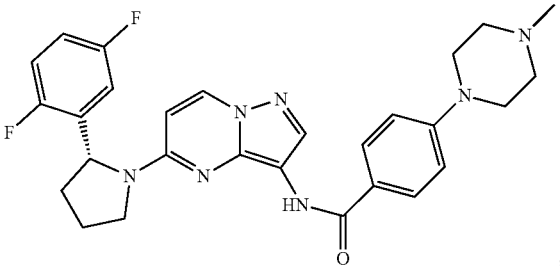,
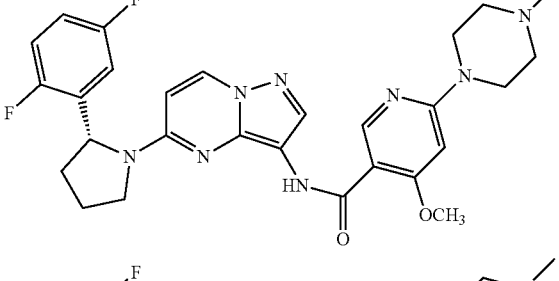,
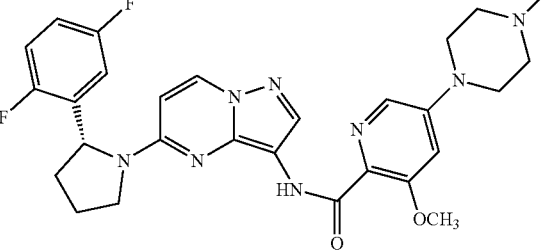,

27

-continued

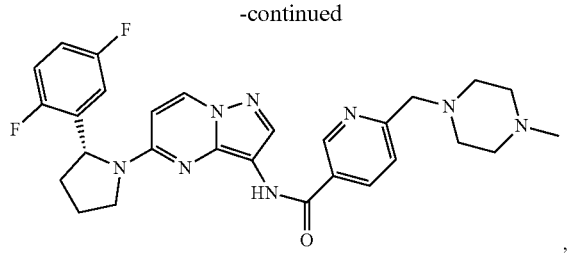
,

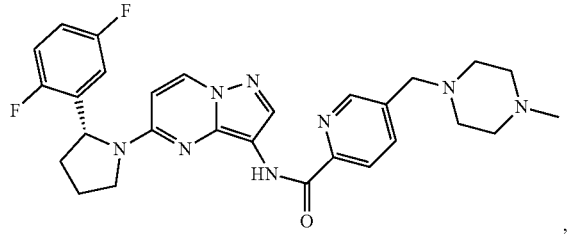
,

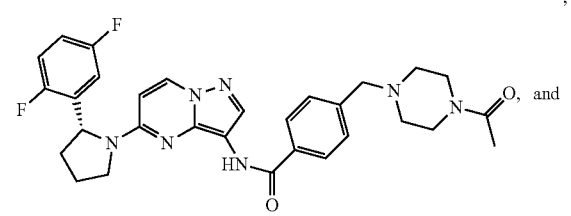
, and

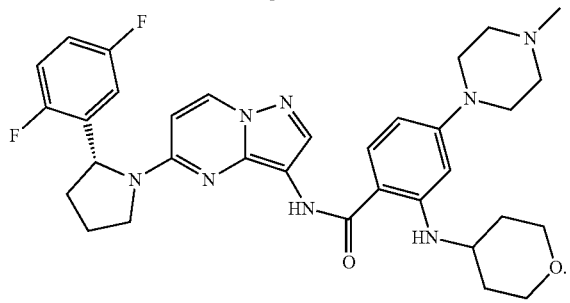
.

In some embodiments of the present disclosure, there are provided pharmaceutical compositions comprising a compound of the present disclosure and a pharmaceutically acceptable carrier.

In some embodiments of the present disclosure, there are provided methods of treating or preventing a hyper-proliferative disorder in a patient, comprising the step of administering to the patient in need thereof a pharmaceutical composition described above.

In some embodiments of the present disclosure, there are provided compounds of the present disclosure for use as a medicament.

In some embodiments of the present disclosure, there are provided compounds of the present disclosure for use as a medicament for treating or preventing a hyper-proliferative disorder.

In some embodiments of the present disclosure, there are provided compounds of present disclosure for use as a medicament for treating or preventing various cancers.

In some embodiments of the present disclosure, there are provided compounds of present disclosure for use in a method of regulating the kinase signaling transduction.

In some embodiments of the present disclosure, there are provided pharmaceutical compositions comprising a compound of present disclosure in combination with one or more anti-cancer agents for use in a method of treating or preventing a hyper-proliferative disorder.

28

In certain embodiments, there are provided compounds without limitation selected from the group consisting of:

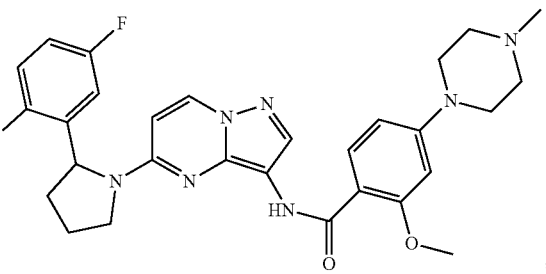
,

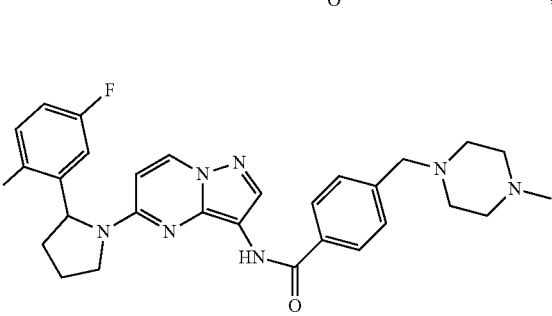
,

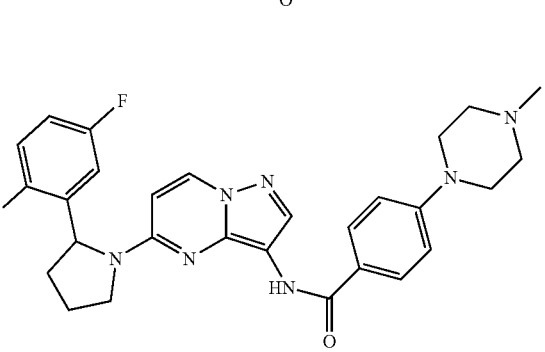

and or a pharmaceutically acceptable salt, solvate, or a prodrug, or a steroisomer, or a metabolite thereof.

In certain embodiments, there are provided compounds without limitation selected from the group consisting of:

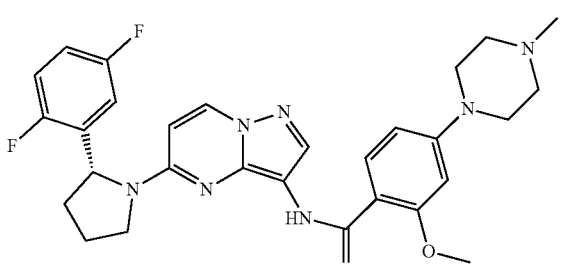
,

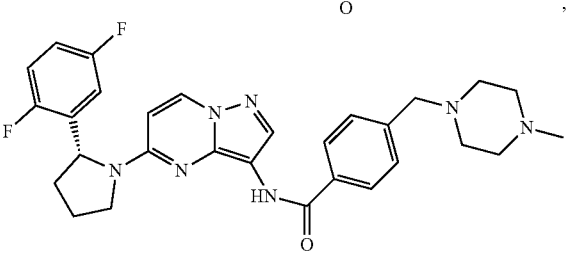
,

-continued

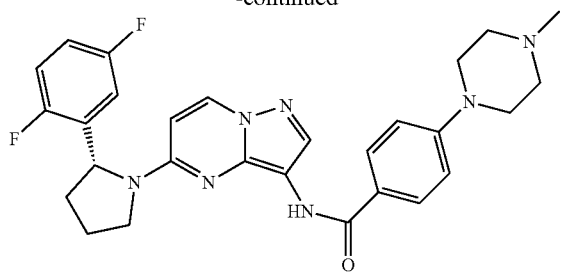

and or a pharmaceutically acceptable salt, solvate, or a prodrug, or a metabolite thereof.

In other embodiments, the compound of this disclosure is in the form of pharmaceutically acceptable salt. In some embodiments, the compound of this disclosure is in the form of a solvate. In other embodiments, the compound of this disclosure is in the form of a metabolite. In other embodiments, the compound of this disclosure is in the form of a prodrug. In some embodiments, the compound of this disclosure is an enantiomer. In other embodiments, the compound of this disclosure is a diastereomer. In another embodiment, the deuterium enrichment in compounds of this disclosure is at least about 1%.

In some embodiments, there are provided pharmaceutical compositions comprising a compound of the disclosure and a pharmaceutically acceptable carrier. In certain embodiments, the compositions are for the treatment of a disease regulated by a protein kinase. In certain embodiments, the compositions are for the prevention or the treatment of a hyper-proliferative disorder and/or angiogenesis disorder. In some embodiments, the pharmaceutical compositions further comprise an anti-neoplastic agent, an immunosuppressant, an immunostimulant, or combination thereof. In other embodiments, the pharmaceutical compositions are suitable for oral, parenteral, or intravenous administration.

In some embodiments, the present disclosure provides methods for regulating the kinase signaling transduction comprising administrating to a mammalian subject a therapeutically effective amount of any of the inventive compounds described herein.

In other embodiments, there are provided herein methods for treating or preventing a tropomyosin-related kinases mediated disorder, said method comprises administrating to a mammalian subject a therapeutically effective amount of any of the inventive compounds described herein.

In other embodiments, there are provided herein methods for treating neoplasia comprising administrating to a mammalian subject in need thereof, a therapeutically effective amount of any of the inventive compounds described herein. In certain embodiments, the neoplasia is selected from skin cancer, leukemia, colon carcinoma, renal cell carcinoma, gastrointestinal stromal cancer, solid tumor cancer, myeloma, breast cancer, pancreatic carcinoma, non-small cell lung cancer, non-Hodgkin's lymphoma, hepatocellular carcinoma, thyroid cancer, bladder cancer, colorectal cancer, and prostate cancer. In some embodiments, the methods further comprise administering one or more anti-cancer agents. In some embodiments, there are provided methods for treating neuroblastoma, ovarian cancer, prostate cancer, pancreatic cancer, large cell neuroendocrine tumors, and colorectal cancer, administrating to a mammalian subject in need thereof, a therapeutically effective amount of a compound of Formula I or Formula II, or a pharmaceutical composition comprising a compound of Formula I or Formula II.

In other embodiments, there are provided Trk inhibitors. As used herein, the term Trk generally refers to tropomyosin receptor kinase or tyrosine receptor kinase. The family of Trk receptors is named for the oncogene trk. Trk, initially identified in a colon carcinoma, is frequently activated in thyroid papillary carcinomas. The oncogene trk is reported to be generated by a mutation in chromosome 1. Normal Trk receptors do not contain amino acid or DNA sequences related to tropomyosin. The three most common types of Trk receptors are TrkA, TrkB, and TrkC, each of which may have different binding affinity to certain types of neurotrophins. Trk receptors are a family of tyrosine kinases that regulates synaptic strength and plasticity in the mammalian nervous system. The differences in the signaling initiated by these distinct types of receptors may generate diverse biological responses. Neurotrophin ligands of Trk receptors may be processed ligands that are synthesized in immature forms and then transformed by protease cleavage Immature neurotrophins may be specific only to one common p75NTR receptor. However, protease cleavage may generate neurotrophins that have higher affinity to their corresponding Trk receptors. These processed neurotrophins may still bind to p75NTR, but may bind at a lower affinity.

In other embodiments, there are provided methods for treating or preventing a hyper-proliferative and/or angiogenesis comprising administrating to a mammalian subject a therapeutically effective amount of any of the inventive compounds described herein.

In other embodiments, there are provided methods for using a pharmaceutical composition of the compound of Formulas I or II to treat mammalian hyper-proliferative disorders, including cancer. The term "hyper-proliferative disorders" and/or "cancer" not only refers to solid tumors, such as cancers of the breast, respiratory tract, brain, reproductive organs, digestive tract, urinary tract, eye, liver, skin, head and neck, thyroid, parathyroid and their distant metastases, but also includes lymphomas, sarcomas, and leukemias.

The following definitions should assist in understanding the disclosure described herein.

The term "alkyl" is intended to include straight, branched, and cyclic hydrocarbon groups, which contain only single carbon-carbon bonds and which may be unsubstituted or optionally substituted with one or more functional groups. The preferred chain length of an alkyl group is from 1 to 6 carbon atoms. $C_1$-$C_6$ alkyl is intended to include $C_1$, $C_2$, $C_3$, $C_4$, $C_5$ and $C_6$ alkyl groups. Alkyl may be substituted or unsubstituted. Typical substituent groups include deuterium, cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^XR^Y$, wherein $R^X$ and $R^Y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring. Illustrative substituted alkyl group include, but are not limited to, $CD_3$, $CD_2CD_3$, fluoromethyl, difluoromethyl, trifluoromethyl, aminomethyl, aminoethyl, hydoxymethyl, methoxymethyl, 2-fluoroethyl, and 2-methoxyethyl, etc.

The term "alkoxy" refers to both an —O-(alkyl) and an —O-(unsubstituted cycloalkyl) group. $C_1$-$C_6$ alkoxy is intended to include $C_1$-$C_6$ alkyl groups, wherein $C_1$-$C_6$ alkyl is defined above. Representative examples include, but are not limited to, $OCD_3$, $OCD_2CD_3$, methoxy, ethoxy, propoxy, butoxy, cyclopropyloxy, cyclobutyloxy, cyclopentyloxy, cyclohexyloxy, and the like.

"Halogen" or "halide" means fluorine, chlorine, bromine, and iodine. "Halo" means fluoro, chloro, bromo, and iodo, preferably fluorine or chlorine.

"Aryl" refers to an all-carbon monocyclic or fused-ring polycyclic groups of 6 to 12 carbon atoms having a completely conjugated 7c-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^XR^Y$, with $R^X$ and $R^Y$ as defined above, Aryl can be also a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrazine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —$NR^XR^Y$ with $R^X$ and $R^Y$ as defined above.

The disclosure also includes isotopically-labeled compounds of the disclosure, wherein one or more atoms is replaced by an atom having the same atomic number, but an atomic mass or mass number different from the atomic mass or mass number usually found in nature. Examples of isotopes suitable for inclusion in the compounds of the disclosure include isotopes of hydrogen, such as deuterium and carbon such as $^{13}C$. Substitution with heavier isotopes such as deuterium may afford certain therapeutic advantages resulting from greater metabolic stability; for example, increased in vivo half-life or reduced dosage requirements, and hence may be preferred in some circumstances.

Deuterium (D or $^2H$) is a non-radioactive, stable isotope of hydrogen, the natural abundance of deuterium is 0.015%. A compound should be considered to be unnatural, if its level of deuterium has been enriched to be greater than the natural abundance level of 0.015%. In a compound of this disclosure, it is understood that the abundance of deuterium is substantially greater than the natural abundance of deuterium, which is 0.015%, when a particular position is designated as deuterium. A position designated as deuterium typically has a minimum isotopic enrichment factor of at least 3000 at each atom designated as deuterium in said compound. The concentration of naturally abundant stable hydrogen is small and immaterial compared to the degree of stable isotopic substitution of compounds of this disclosure.

The term "pharmaceutically acceptable" when used with reference to a compound of the disclosure is intended to refer to a form of the compound that is safe for administration to a subject. For example, a free base, a salt form, a solvate, a hydrate, a prodrug or derivative form of a compound of this disclosure, which has been approved for mammalian use, via oral ingestion or any other route of administration, by a governing authority or regulatory agency, such as the Food and Drug Administration (FDA) of the United States, is pharmaceutically acceptable.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Starting materials of the disclosure, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described below.

In synthesizing a compound of Formula I or Formula II according to a desired procedure, the steps in some embodiment, are performed in an order suitable to prepare the compound, including a procedure described herein or by an alternate order of steps described herein, and in one embodiment, be preceded, or followed, by additional protection/deprotection steps as necessary. The intermediates in some embodiments are isolated or carried on in situ, with or without purification. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of this disclosure in some embodiments also are represented in multiple tautomeric forms. The disclosure expressly includes all tautomeric forms of the compounds described herein.

The compounds in one embodiment also occur in cis- or trans- or E- or Z-double bond isomeric forms. All such isomeric forms of such compounds are expressly included in the present disclosure.

Indication

The present disclosure provides compounds which are capable of modulating one or more signal transduction pathways comprising, but not limited to tropomyosin-related kinase.

By the term "modulating," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present disclosure can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present disclosure possess the ability to modulate kinase activity. The methods of the present disclosure, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Formulations and Method of Use

The amount of compound(s) which is/are administered and the dosage regimen for treating cancer with the compounds and/or compositions of this disclosure depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg may be appropriate, and should be useful for all methods of use disclosed herein. The daily dose can be administered in one to four doses per day.

While it may be possible to administer a compound of the disclosure alone, in the methods described, the compound administered normally will be present as an active ingredient in a pharmaceutical composition. Thus, in another embodiment of the disclosure, there is provided a pharmaceutical composition comprising a compound of this disclosure in combination with a pharmaceutically acceptable carrier, which includes diluents, excipients, adjuvants and the like (collectively referred to herein as "carrier" materials) as described herein, and, if desired, other active ingredients. A pharmaceutical composition of the disclosure may comprise an effective amount of a compound of the disclosure or an effective dosage amount of a compound of the disclosure. An effective dosage amount of a compound of the disclosure includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

The compounds of the disclosure may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

Formulations for parenteral administration may be formulated to be immediate and/or modified release. Modified release formulations include delayed-, sustained-, pulsed-, controlled-, targeted and programmed release. Thus compounds of the disclosure may be formulated as a solid, semi-solid, or thixotropic liquid for administration as an implanted depot providing modified release of the active compound. Examples of such formulations include drug-coated stents and PGLA microspheres.

Combinations

While the compounds of the disclosure can be dosed or administered as the sole active pharmaceutical agent, they can also be used in combination with one or more compounds of the disclosure or in conjunction with other agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula I or Formula II is co-administered with a second therapeutic agent, wherein the compound of Formula I or Formula II and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula I or Formula II is initiated prior to, during, or after treatment with a second agent described herein, and continues until any time during treatment with the second agent or after termination of treatment with the second agent. It also includes treatments in which a compound of Formula I or Formula II and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

The compounds of Formula I or Formula II as well as combination therapies that include compounds of Formula I or Formula II, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Specifically, the administration of compounds of the present disclosure in some embodiments are in conjunction with additional therapies known to those skilled in the art in the prevention or treatment of cancer.

Synthesis of Compounds

The compounds of Formula I or Formula II were synthesized according to the procedures described in the following Schemes to those skilled in the art, wherein the substituents are as defined for Formula I or Formula II above, except where further noted. The synthetic methods described below are merely exemplary, and the compounds of the disclosure may also be synthesized by alternate routes as appreciated by persons of ordinary skill in the art.

The synthesis of compounds of Formula II in the disclosure was described in the Scheme 1. The Acylation reaction of Compound 1 with ArCOCl or ArCOOH afforded Compounds in Formula II or Formula I (Scheme 1).

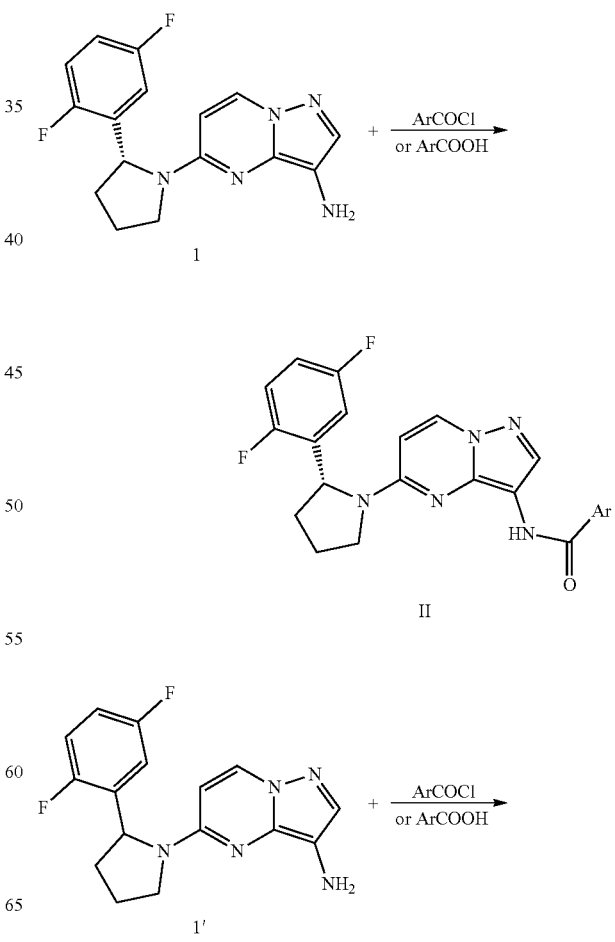

-continued

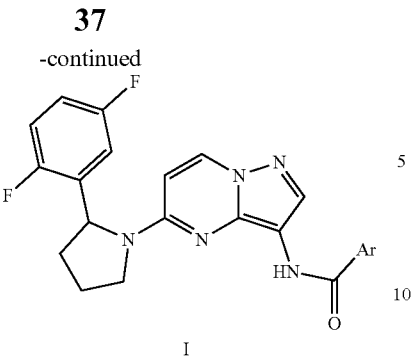

I

DESCRIPTION OF EMBODIMENTS

These detailed descriptions are presented for illustrative purposes only and are not intended as a restriction on the scope of the claims.

Proton NMR Spectra

Unless otherwise indicated, all $^1$H NMR spectra were run on a Varian series Mercury 300, 400 MHz instrument or a Bruker series 400 MHz instrument. Where so characterized, all observed protons are reported as parts-per-million (ppm) downfield from tetramethylsilane (TMS) or other internal reference in the appropriate solvent indicate.

Abbreviation

DCM means dichloromethane.

RT means room temperature.

EA means ethyl acetate.

DIPEA means N,N-diisopropylethylamine

TLC means thin-layer chromatography.

HATU means 1-[bis(dimethylamino)methylene]-1H-1,2,3-triazolo[4,5-b]pyridinium 3-oxide hexafluorophosphate or hexafluorophosphate azabenzotriazole tetramethyl uranium.

EXAMPLES OF SYNTHESIS

Example 1: Synthesis of (R)-5-(2-(2,5-difluorophenyl)pyrrolidin-1-yl)pyrazolo[1,5-a]pyrimidin-3-amine

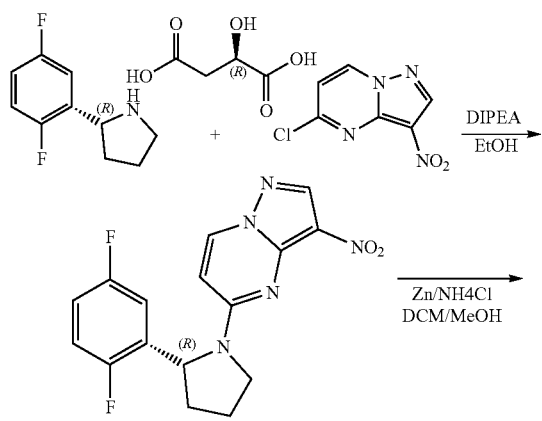

-continued

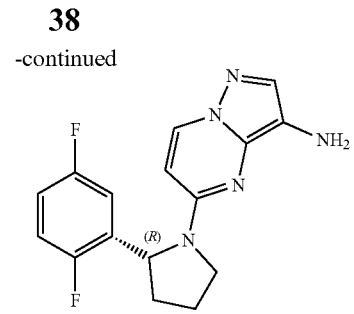

Step 1: Synthesis of (R)-5-(2-(2,5-difluorophenyl)pyrrolidin-1-yl)-3-nitropyrazolo[1,5-a]pyrimidine (R)-2-(2,5-difluorophenyl)pyrrolidine (R)-2-hydroxysuccinate (17.6 g, 5.5 mmol, 1.1 eq), 5-chloro-3-nitropyrazolo[1,5-a]pyrimidine (10.0 g, 5.0 mmol, 1.0 eq) and ethanol was added to a round bottom flask outfitted with a mechanical stirrer. After dissolution, DIPEA (22.7 g, 17.6 mmol, 3.5 eq) was added to the reaction mixture at room temperature. The reaction was stirred at room temperature for 3 hours. Filtered and the cake was washed with ethanol (30 ml×2). Dried at 40° C. to give the product (11.3 g).

Step 2: Synthesis of (R)-5-(2-(2,5-difluorophenyl)pyrrolidin-1-yl)pyrazolo[1,5-a]pyrimidin-3-amine To a round bottom flask equipped with mechanical stirrer, (R)-5-(2-(2,5-difluorophenyl)pyrrolidin-1-yl)-3-nitropyrazolo[1,5-a]pyrimidine (50.0 g, 145 mmol, 1.0 eq) was added and followed by an addition of methanol/DCM (625 ml/625 ml). After dissolution, Zn (94.2 g, 1.45 mol, 10.0 eq) was added to the reaction mixture. The temperature of the reaction was adjusted to between 25° C. to 30° C. At this temperature, saturated ammonium chloride aqueous (657 ml) was added dropwise to the reaction mixture and stirred for 3 hours. The reaction was monitored by TLC.

The reaction mixture was then filtered over a bed of celite. The filter bed was washed with DCM (200 ml×2), separated and the water phase was extracted with DCM (250 ml×2). Separated and combined with organic layers, dried over anhydrous sodium sulfate. Evaporated by vacuum and purified by flash silica gel column chromatography to give the product (51 g)

Example 2: Synthesis of (R)—N-(5-(2-(2,5-difluorophenyl)pyrrolidin-1-yl)pyrazolo[1,5-a]pyrimidin-3-yl)-4-((4-methylpiperazin-1-yl)methyl)benzamide

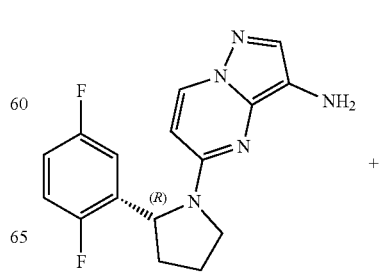

+

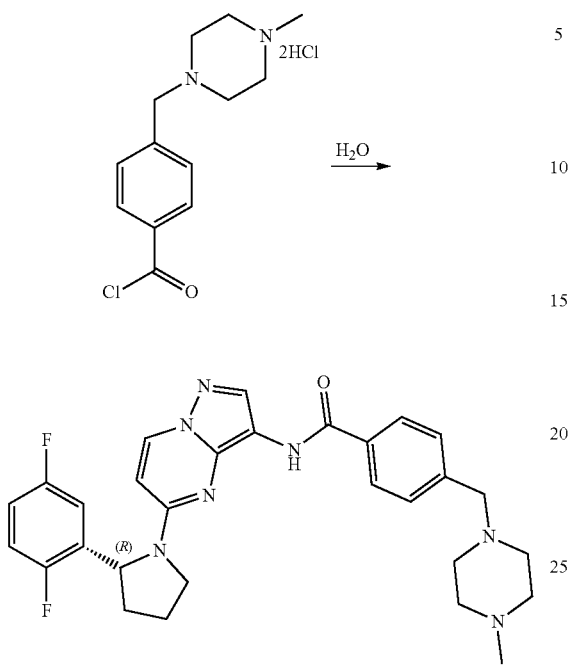

Water and (R)-5-(2-(2,5-difluorophenyl)pyrrolidin-1-yl)pyrazolo[1,5-a]pyrimidin-3-amine (46.4 g, 147.2 mmol, 1.0 eq) was mixed together. The temperature of the mixture was adjusted to between 0° C. to 5° C. At this temperature range, 4-((4-methylpiperazin-1-yl)methyl)benzoyl chloride dihydrochloride (95.9 g, 294.4 mmol, 2.0 eq) was added to the mixture via 5 portions, with each portion added to the mixture in every 10 minutes.

After completion of the reaction, activated charcoal (5.0 g) was added to the reaction mixture and the reaction mixture was stirred for 15 minutes. The reaction mixture was then filtered over a bed of celite. The filter bed was washed with water (100 ml×2).

The filtrate was extracted with EA (200 ml×2), followed by extraction with DCM/EA (v/v=3:7, 200 ml×3), last the filtrate was extracted with EA (200 ml) again. The aqueous phase was heated to 50-55° C., then the pH of reaction solution was adjusted to 9-10 with aqueous NaOH (20%). It was extracted with EA (250 ml), some precipitates were formed, which were filtered and separated. The aqueous phase was extracted with EA (200 ml×2). The organic layers were combined.

Activated charcoal (5.0 g) was added to the organic layer, then the reaction mixture was heated to 50-55° C. and stirred for 30 minutes. The reaction mixture was then filtered over a bed of celite. The filter bed washed with EA (100 ml×3), the filtrate was dried over anhydrous sodium sulfate. Evaporated by vacuum at 40° C. to give the product (71.3 g) as a yellow solid.

$^1$HNMR(CDCl$_3$): 2.08 (s, 3H), 2.32 (d, J=10.0, 6H), 2.48-2.51 (m, 8H), 3.59 (s, 2H), 4.12 (s, 1H), 6.01 (brs, 1H), 6.78 (s, 1H), 6.91-6.93 (m, 1H), 7.01-7.04 (m, 1H), 7.47 (d, J=8.4, 2H), 7.88 (d, J=6.8, 2H), 8.16 (d, J=7.2, 2H), 8.64 (s, 1H). MS m/z 532 [M+1].

Example 3: Synthesis of (R)—N-(5-(2-(2,5-difluorophenyl)pyrrolidin-1-yl)pyrazolo[1,5-a]pyrimidin-3-yl)-2-methoxy-4-(4-methylpiperazin-1-yl) benzamide

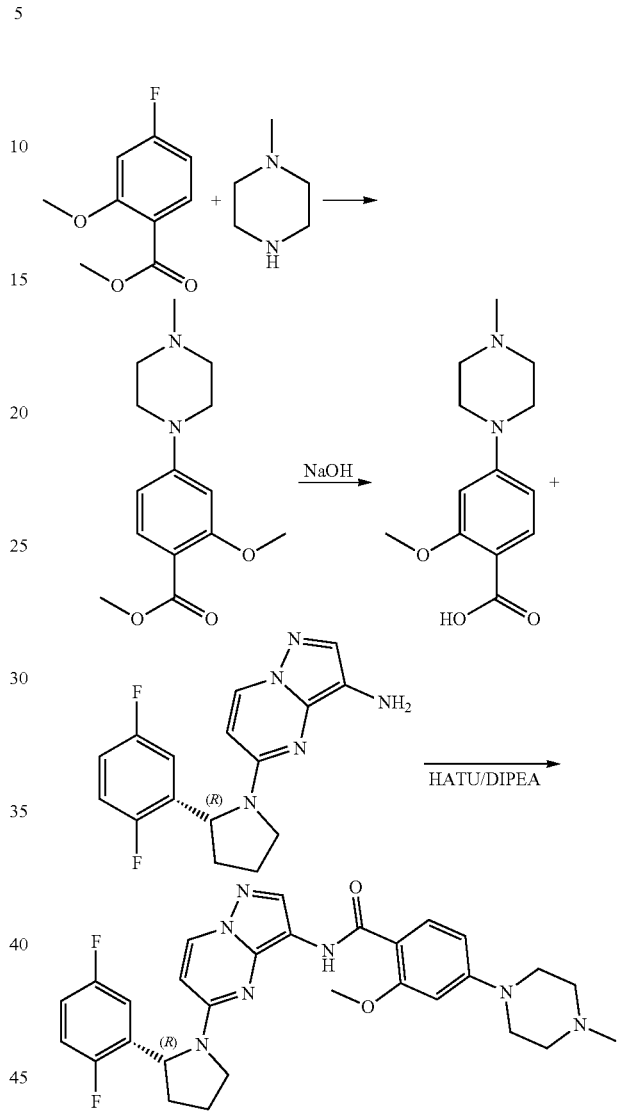

Step 1: Synthesis of methyl 2-methoxy-4-(4-methylpiperazin-1-yl)benzoate

A mixture of methyl 4-fluoro-2-methoxybenzoate (1.84 g, 10.0 mmol, 1.0 eq) and 1-methylpiperazine (2.0 g, 20.0 mmol, 2.0 eq) was added to a 100 ml three-neck round bottom flask. The reaction was heated to 80° C. and stirred for 40 hours. Then water (20 ml) was poured into the reaction solution, and the mixture was extracted with ethyl acetate (20 ml×3), and the organic layers were combined and dried over anhydrous sodium sulfate. Evaporation under vacuum at 45° C. gave a yellow oil. The yellow oil was dissolved with DCM (30 ml), HCl in isopropanol (30%, 4 ml) was added to the reaction solution, some solids appeared. The solids were collected by filtration and the collected solids were washed with DCM (10 ml×2) to give a crude product 1.32 g.

Step 2: Synthesis of 2-methoxy-4-(4-methylpiperazin-1-yl)benzoic acid

Methyl 2-methoxy-4-(4-methylpiperazin-1-yl)benzoate (200 mg, 0.66 mmol, 1.0 eq) and MeOH (5.0 ml) was added to a 100 ml Three-neck round bottom flask. Stirred and NaOH aqueous (4 mol/L, 5.0 ml) was added to the reaction solution. The reaction solution was heated at 60° C. for 3 hours. The reaction was monitored by TLC. The methanol was removed under vacuum at 45° C. and the pH of the remaining mixture was adjusted to 6 with HCl aqueous (4 mol/L), then extracted with n-BuOH (10 ml×3). The organic layers were collected, dried over anhydrous sodium sulfate. Evaporation under vacuum gave the product (60 mg).

Step 3: Synthesis of (R)—N-(5-(2-(2,5-difluorophenyl)pyrrolidin-1-yl)pyrazolo[1,5-a]pyrimidin-3-yl)-2-methoxy-4-(4-methylpiperazin-1-yl)benzamide A mixture of 2-methoxy-4-(4-methylpiperazin-1-yl)benzoic acid (50.0 mg, 0.17 mmol, 1.0 eq), (R)-5-(2-(2,5-difluorophenyl)pyrrolidin-1-yl)pyrazolo[1,5-a] pyrimidin-3-amine (55.0 mg, 0.17 mmol, 1.0 eq) and HATU (79.2 g, 0.21 mmol, 1.2 eq) was dissolved in DCM (5 ml). DIPEA (45.2 mg, 0.35 mmol, 2.0 eq) was added to the reaction mixture. The reaction mixture was stirred at room temperature for 3 hours. Water (20 ml) was added to the reaction mixture, extracted with DCM (10 ml×3). The organic layers were combined, dried over anhydrous sodium sulfate. Evaporation under vacuum afforded a crude which was purified by silica gel column chromatography to give the product (20 mg) as a yellow solid. $^1$HNMR (CDCl$_3$):2.11-2.12 (m, 4H), 2.40 (s, 3H), 2.48 (s, 1H), 2.62 (t, $J_1$=5.2, $J_2$=5.2, 4H), 3.39 (t, $J_1$=4.8, $J_2$=5.2, 4H), 3.80 (s, 1H), 4.02 (s, 3H), 4.01 (s, 1H), 6.0 (brs, 1H), 6.45 (s, 1H), 6.65 (dd, $J_1$=2.0, $J_2$=8.8, 1H), 6.75-6.79 (m, 1H), 6.93-6.95 (m, 1H), 7.04-7.06 (m, 1H), 8.20 (d, J=8.8, 2H), 8.76 (s, 1H), 8.89 (brs, 1H). MS m/z 548 [M+1].

Example 4: Synthesis of (R)—N-(5-(2-(2,5-difluorophenyl)pyrrolidin-1-yl)pyrazolo[1,5-a]pyrimidin-3-yl)-4-(ethylsulfonamido)benzamide

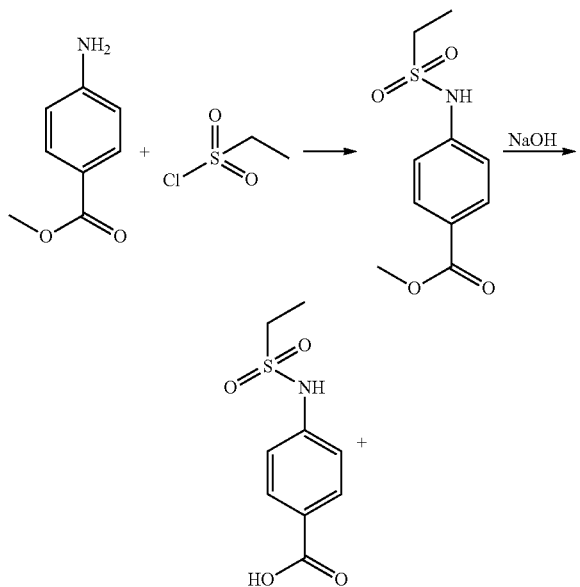

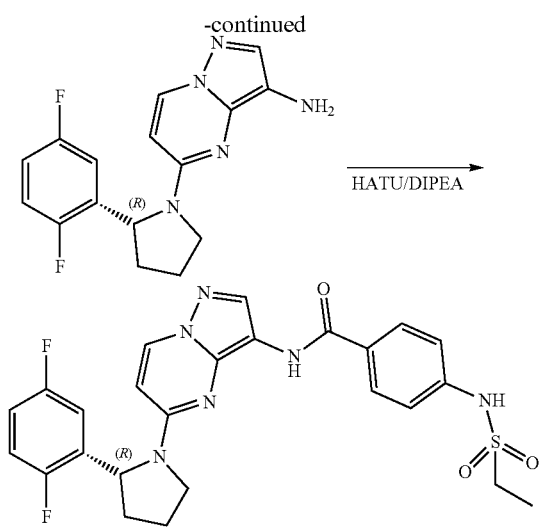

Step 1: Synthesis of methyl 4-(ethylsulfonamido)benzoate

Methyl 4-aminobenzoate (2.0 g, 13.2 mmol, 1.0 eq) was dissolved in DCM (15 ml), stirred and pyridine (2.1 g, 26.4 mmol, 2.0 eq) was added to the reaction mixture. The reaction mixture was cooled to 0-5° C. with ice bath. Then ethanesulfonyl chloride (2.0 eq, 15.8 mmol, 1.2 eq) was added dropwise to the reaction mixture, and the temperature of the reaction was kept no more than 10° C. The reaction was warmed to room temperate and kept for 3 hours. The reaction mixture was poured into water, some solids appeared. The solids were collected by filtration and the collected solids were washed with water (20 ml×2) to give the product wet (4.6 g).

Step 2: Synthesis of 4-(ethylsulfonamido)benzoic acid

Methyl 4-(ethylsulfonamido)benzoate (2.3 g, wet) and MeOH (15 ml) were added to a 100 ml three-neck round bottom flask. The reaction mixture was stirred with ice bath. NaOH aqueous (15 ml) was added dropwise to the reaction mixture at 0-5° C. Then the reaction was allowed to warm to room temperature and kept for 6 hours. The methanol was removed under vacuum at 45° C. and the remaining mixture was treated with HCl (conc.) to adjust its pH to 2). Some solids appeared. The solids were collected by filtration and the collected solids were washed with water to give the product wet (1.3 g), kept at room temperature overnight.

Step 3: Synthesis of (R)—N-(5-(2-(2,5-difluorophenyl)pyrrolidin-1-yl)pyrazolo[1,5-a]pyrimidin-3-yl)-4-(ethylsulfonamido)benzamide A mixture of 4-(ethylsulfonamido)benzoic acid (144.5 mg, 0.63 mmol, 1.0 eq), (R)-5-(2-(2,5-difluorophenyl)pyrrolidin-1-yl)pyrazolo[1,5-a]pyrimidin-3-amine (200 mg, 0.63 mmol, 1.0 eq) and HATU (287.3 mg, 0.76 mmol, 1.2 eq) were dissolved in DCM (10 ml), and DIPEA (162.5 mg, 1.26 mmol, 2.0 eq) was added to the reaction mixture. The reaction mixture was stirred at room temperature for 1 hour. Water (15 ml) was added to the reaction mixture. The organic layer was separated, and the aqueous layer was extracted with DCM (10 ml). The organic layers were combined, dried over anhydrous sodium sulfate. Evaporated under vacuum and purification by silica gel column chromatography gave the product (240.9 mg) as a yellow solid. LC-MS (M+1=527.2).

$^1$HNMR (CDCl$_3$):1.41 (t, J=7.2, 3H), 2.02-2.12 (m, 5H), 2.51-2.52 (m, 1H), 3.22(q, J$_1$=7.6, J$_2$=7.2, 2H), 3.951 (s, 1H), 6.0 (brs, 1H), 6.79 (s, 1H), 6.91 (s, 1H), 7.03 (s, 1H), 7.33-7.36 (d, J=8.4, 2H), 7.70 (s, 1H), 7.88-7.90 (d, J=7.2, 2H), 8.21 (s, 2H), 8.61 (s, 1H). MS m/z 527 [M+1].

Biological Assays:

Kinase Assays:

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

Other Assays:

Compounds 1~4 are assayed:

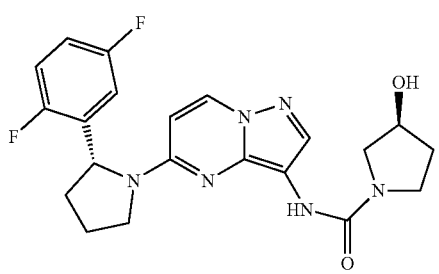

Compound 1 (LOXO-101) is

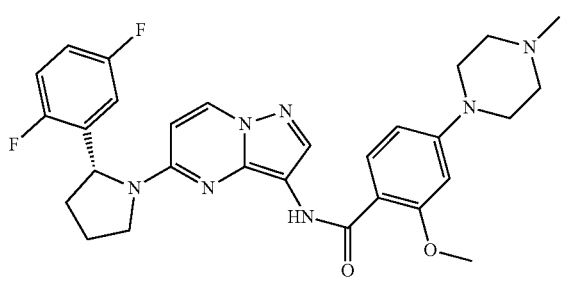

Compound 2 is

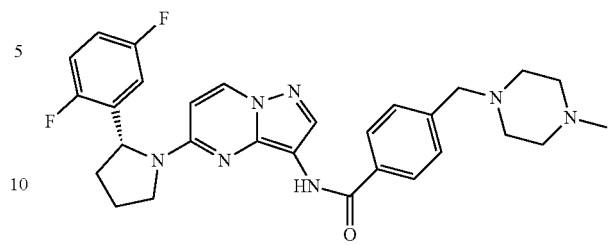

Compound 3 is

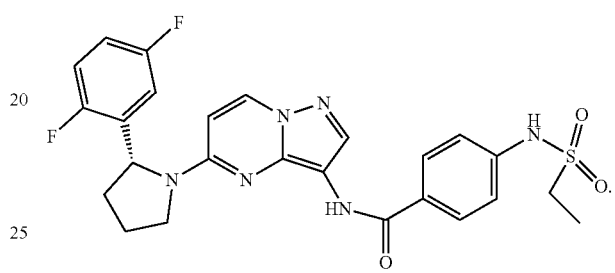

Compound 4 is (a) An In Vitro Assay which Determines the Ability of a Test Compound to Inhibit Kinase Activity I. Prepare 1× Kinase Base Buffer and Stop Buffer for Testing Kinases 1) 1× Kinase base buffer (for TRK-A)
50 mM HEPES, pH 7.5
0.0015% Brij-35

2) Stop buffer
100 mM HEPES, pH 7.5
0.015% Brij-35
0.2% Coating Reagent #3
50 mM EDTA II. Prepare Source Plate with Compound 1) Dilute the compound to 50× of the final concentration in reaction by 100% DMSO. Transfer 100 µl of this compound dilution to a well in a 96-well plate. For example, if the desired highest inhibitor concentration is 10 µM, then prepare a 500 µM of compound DMSO solution in this step.

2) Perform 3× series dilution of the compound dilution obtained in step 1) with 100% DMSO to provide 9 more diluted solutions of the compound.

3) Add 100 µl of 100% DMSO to two empty wells for no compound control and no enzyme control in the same 96-well plate. Mark the plate as source plate.

4) Prepare intermediate plate
Transfer 10 µl of compound from the source plate to a new 96-well plate as the intermediate plate.
Add 90 µl of 1× Kinase base buffer to each well of the intermediate plate.
Mix the compounds in intermediate plate for 10 mM on a shaker.

5) Prepare assay plate
Transfer 5 µl of each well from the 96-well intermediate plate to a 384-well plate in duplicates. For example, A1 of the 96-well plate is transferred to A1 and A2 of the 384-well plate. A2 of the 96-well plate is transferred to A3 and A4 of the 384-well plate, and so on.

III. Kinase Reaction

1) Prepare 2.5× enzyme solution Add kinase in 1× kinase base buffer.

2) Prepare 2.5× peptide solution

Add FAM-labeled peptide (SEQ ID NO:1) and ATP in the 1× kinase base buffer.

3) Transfer 2.5× enzyme solution to the assay plate

Assay plate already contains 5 µl of the compound in 100% DMSO.

Add 10 µl of 2.5× enzyme solution to each well of the 384-well assay plate.

Incubate at room temperature for 10 min

4) Transfer 2.5× peptide solution to the assay plate

Add 10 µl of 2.5× peptide solution to each well of the 384-well assay plate.

5) Kinase reaction and stop

Incubate at 28° C. for a specified period of time.

Add 25 µl of Stop buffer to stop reaction.

IV. Caliper Reading

Collect data on Caliper.

V. Curve Fitting

Copy conversion data from Caliper program.

Convert conversion values to inhibition values.

Percent inhibition=(max−conversion)/(max−min)*100.

"max" stands for DMSO control; "min" stands for no enzyme activity control.

Fit the data in Xlfit to obtain IC50 values.

Equation used is $Y = Bottom + (Top - Bottom)/(1 + 10^{((LogIC50 - X)*Hill\ Slope)})$ The following Table A lists compounds representative of the disclosure and their activity in ROS1 and TRK-A assays, both of which are kinase assays generally described above.

TABLE A

| Compound | TRK-A IC$_{50}$ | ROS-1 IC$_{50}$ |
|---|---|---|
| 2 | 1.8 nM | NA |
| 3 | 3.0 nM | 104 nM |

(b) A Representative Number of Compounds were Assayed Against TEL-NTRK1-BaF3 Cell.

I. Prepare Compound Plate

Compounds to be assayed were dissolved in 100% DMSO to prepare a 4 mM mother solution, which underwent 3× series dilution to prepare solutions with concentrations of 10 mM, 3.333 mM, 1.111 mM, 0.370 mM, 0.123 mM, 0.041 mM, 0.014 mM, all of which stored in 0.5 mL sterile eppendorf (Corning, N.Y., USA). At the same time prepare a blank sample as control containing DMSO only with the same volume as the compound solutions. The 9 samples on the Compound plate were store at −20° C. in vacuum.

II. Cell Culture Conditions

TEL-NTRK1-BaF3 cell line was cultured in RPMI 1640 (Corning, N.Y., USA)+10% fetal calf serum (Gibco/Invitrogen, USA) for two generations after resuscitation. Stored for future use.

III. Assay and Data Analysis

Cells (2,000-2,500 cells per well) at log phase were harvested and inoculated in wells of a white, opaque cell culture plate (Corning 3570, NY, USA). The volume of suspensions comprising cells in each well was 100 µL. Compounds from the Compound plate were added 0.1 µL per well to the cell culture plate to reach a final compound concentrations of 10 µM, 3.3 µM, 1.1 µM, 0.37 µM, 0.12 µM, 0.04 µM, and 0.014 µM. Incubated at 37° C. and 5% $CO_2$ culture chamber for 72 hours. Ten µL CellTiter-Glo® Luminescent Cell Viability Assay Reagent was added to each well, wait for 10 minutes, then read using Evision Plate-Reader.

The following Table B lists compounds representative of the disclosure and their activity in TEL-NTRK1-BaF3 Cell assay.

TABLE B

| | TEL-NTRK1-BaF3 GI50 (nM) |
|---|---|
| LOXO-101 | 25 |
| Compound 2 | <1 |
| Compound 3 | 3 |
| Compound 4 | 24 |

(c) Solubility Measurement of a Representative Number of Compounds

Solubility measurement procedure may include:

Preparation of reference standard solution: 2 mg of the testing compound was added individually to 100 mL volumetric flask each. The compound was diluted with acetonitrile to 100 mL.

Preparation of sample solution: 2 mg of the testing compound was added individually to 2 mL eppendorf tube (EP), followed by the addition of 1 mL of pH 4.0 buffer solution (20 mM). The solution was shaken for 2 minutes and left for 30 minutes at 25° C. After standing for 30 minutes, precipitate was formed at the bottom of the EP. The solution was filtered through a 0.2 µm membrane filter, and then diluted by 50 times with water.

The standard and sample solutions were injected into the HPLC on a Shim-Pack CLC-ODS $C_{18}$ column (150 mm×6.0 mm, Sum) with the same volume. The mobile phase consists of acetonitrile with 2% trichloromethane—20 mM $KH_2PO_4$ buffer (pH=7.0) at a flow rate of 1 mL/minutes (40:60). The detection wavelength was at 264 nm. Calculation: solubility of sample=the concentration of standard×Area of sample× 50/Area of standard.

The following Table C lists solubility data for selected compounds.

TABLE C

| | LOXO-101 | Compound 3 | Compound 4 |
|---|---|---|---|
| Solubility at pH 4.0 | 0.31 mg/mL | 36.10 mg/mL | 0.31 mg/mL |

(d) Pharmacokinetic Study of a Representative Number of Compounds

A representative protocol for the PK (pharmacokinetic) assay was as followed: Compounds were given either IV or orally to the same animals. The dose for each compound was 2 mg/kg (volume 5 ml/kg) IV and 5 mg/kg (volume 10 ml/kg) orally. The formulation for IV was in 10% Solutol HS 15+90% Phosphate-Buffered Saline at 0.4 mg/mL. A 100% (0.5% Tween 80 in 0.5% MC in water) at 0.5 mg/mL suspension was used for the oral formulation.

Sample collection: for the IV route, plasma sample were collected at the time points of 0.083, 0.25, 0.5, 1, 2, 4, 8 and 24 hr. For the oral route, plasma sample were collected at the time points of 0.25, 0.5, 1, 2, 4, 8 and 24 hr.

Analysis: LC-MS/MS was used to calculate PK parameters: t1/2, tmax, Cmax, Vss and AUC, etc.

The following TABLE D lists selected compounds and their bioavailability.

TABLE D

| Compound | F (%) |
|---|---|
| LOXO-101 | 33 |
| 3 | 56 |

In rat Compound 1 or LOXO-101 demonstrated 33% oral bioavailability. surprisingly, Compound 3 has much improved bioavailability (F=56%).

Compound 1 (LOXO-101) had low brain penetration, In contrast, both Compounds 2 and 3 have very high brain to plasma ratio (0.96 and 5.47, respectively), indicating that Compounds 2 and 3 can penetrate the blood brain barrier.

(e) Toxicity Studies

A representative number of compounds, including Compound 1 (LOXO-101) and Compound 3, were tested in a typical one-month toxicity studies in rat with dosages of 30 mg/kg and 100 mg/kg. Under the conditions of this experiment, at the end of the compound administration period and the end of the recovery period, some animals in the group administered with LOXO-101 at 30 mg/kg and 100 mg/kg dosages displayed slight decrease in #LYMPH and/or % LYMPH in blood, and a slight increase trend in #NEUT and/or % NEUT in blood. The corresponding animal bone marrow displayed increase or trend for increase in myeloid: erythroid ratio. In contract, similar changes were not observed in the Compound 3 treatment group at 30 mg/kg or 100 mg/kg dosages or the vehicle control group.

or a pharmaceutically acceptable salt, solvate, stereoisomer, or tautomer thereof, wherein Ar is

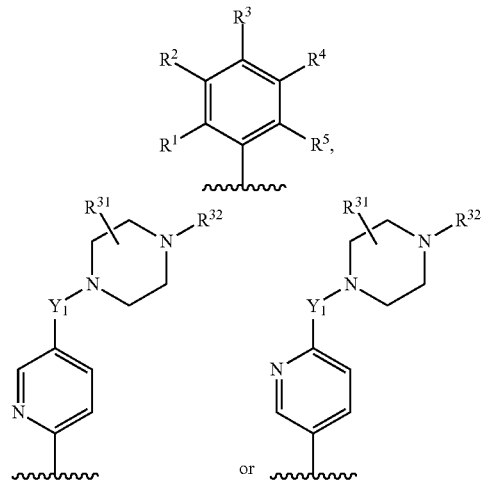

wherein at least one of $R^1$, $R^2$, $R^3$, $R^4$, and $R^5$ is not hydrogen, each of $R^1$, $R^2$, $R^3$, $R^4$, and $R^5$ is independently hydrogen, halide, $C_1$-$C_6$ alkyl, $C_1$-$C_6$alkyloxy, $C_2$-$C_6$alkenyl, $C_2$-$C_6$alkynyl, $C_3$-$C_6$cycloalkyl, $C_6$-$C_{12}$

The invention claimed is:

1. A compound according to Formula I:

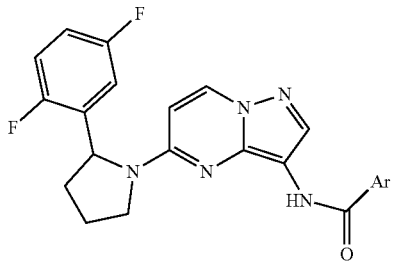

I aryl, 3-12 membered heteroalicyclic, 5-12 membered heteroaryl, $NO_2$, $-NR^6R^7$, $-CR^8R^9(CR^8R^9)_nOR^6$, CN, $-C(O)R^6$, $-O(CO)R^6$, $-OCR^8R^9(CR^8R^9)_nNR^6R^7$, $-OCR^8R^9(CR^8R^9)_nOR^6$, $-NR^6C(O)R^7$, $-(CR^8R^9)_nC(O)OR^6$, $-(CR^8R^9)_nC(O)NR^6R^7$, $-CR^8R^9(CR^8R^9)_nNR^6R^7$, $-NR^6(CO)-NR^6R^7$, $-S(O)_tR^6$, or $-S(O)_2NR^6R^7$, wherein two groups among $R^1$, $R^2$, $R^3$, $R^4$, and $R^5$ on adjacent atoms of the phenyl may, together with the adjacent atoms to which two groups are bound, be combined to form a $C_6$-$C_{12}$ aryl, 5-12 membered heteroaryl, $C_3$-$C_{12}$ cycloalkyl or 3-12 membered heteroalicyclic, wherein each aryl, heteroalicyclic, and heteroaryl is unsubstituted or independently substituted with one or more deuterium or $C_1$-$C_3$ alkyl; with the proviso that the heteroatom of 3-12 membered heteroalicyclic is not attached to the phenyl;

each of $R^6$, $R^7$, $R^8$, and $R^9$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^6$, $R^7$, $R^8$, and $R^9$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^6$, $R^7$, $R^8$, and $R^9$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;

each n is independently 0, 1, 2, 3, or 4;
each p is independently 1 or 2;
each t is independently 0, 1, or 2;
$Y_1$ is a bond or $CR^{23}R^{24}$;
$R^{31}$ is one or more groups independently selected from the group consisting of hydrogen, $C_1$-$C_3$ alkyl and deuterium;
$R^{32}$ is $C_1$-$C_3$ alkyl, $CO(C_1$-$C_3$ alkyl) or hydrogen; and
each of $R^{23}$ and $R^{24}$ is independently hydrogen, deuterium, or $C_1$-$C_3$ alkyl.

2. The compound of claim 1, wherein the compound is according to Formula II:

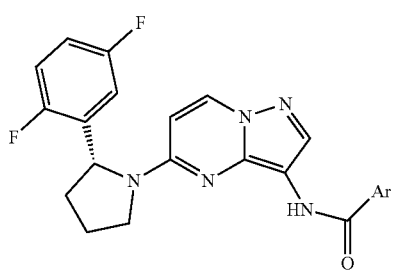

II or a pharmaceutically acceptable salt, solvate, stereoisomer, or tautomer thereof, wherein Ar is defined as in claim 1.

3. A compound according to Formula I:

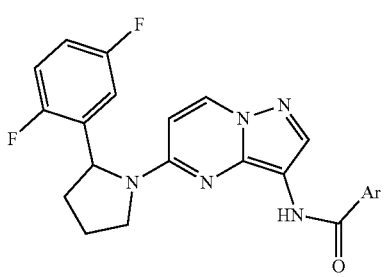

I or a pharmaceutically acceptable salt, solvate, stereoisomer, or tautomer thereof, wherein Ar is:

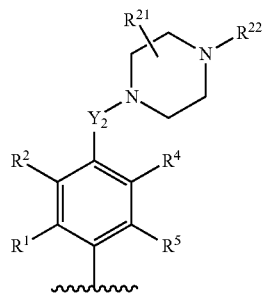

wherein $Y_2$ is a bond or $CR^{23}R^{24}$;
each of $R^1$, $R^2$, $R^4$, and $R^5$ is independently hydrogen, halide, $CF_3$, $C_1$-$C_3$ alkyl, $NO_2$, $C_1$-$C_3$alkoxyl, or oxan-4-ylamino;
$R^{21}$ is one or more groups independently selected from the group consisting of hydrogen, $C_1$-$C_3$ alkyl and deuterium;
$R^{22}$ is $C_1$-$C_3$ alkyl, $CO(C_1$-$C_3$ alkyl) or hydrogen; and
each of $R^{23}$ and $R^{24}$ is independently hydrogen, deuterium, or $C_1$-$C_3$ alkyl.

4. The compound of claim 1, Ar is:

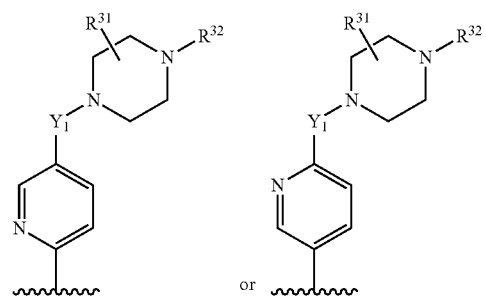

wherein $Y_1$ is a bond or $CR^{23}R^{24}$;
$R^{31}$ is one or more groups independently selected from the group consisting of hydrogen, $C_1$-$C_3$ alkyl and deuterium;
$R^{32}$ is $C_1$-$C_3$ alkyl, $CO(C_1$-$C_3$ alkyl) or hydrogen; and
each of $R^{23}$ and $R^{24}$ is independently hydrogen, deuterium, or $C_1$-$C_3$ alkyl.

5. The compound of claim 1, wherein the compound is selected from the group consisting of:

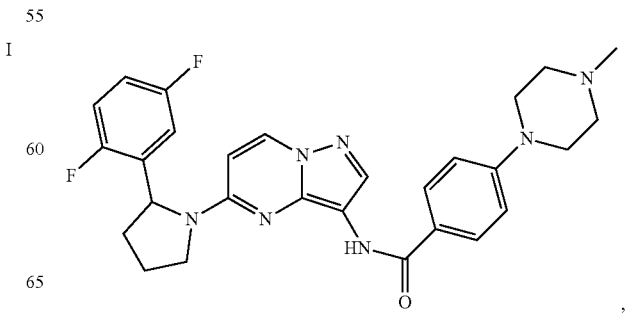

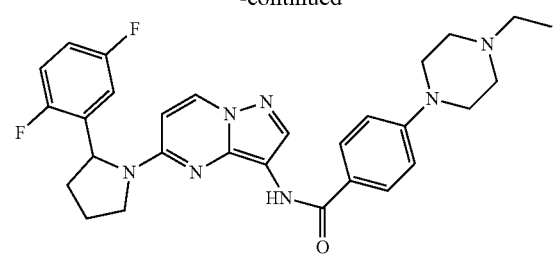
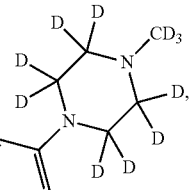
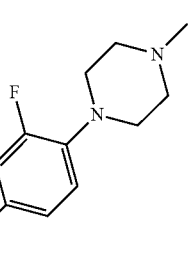
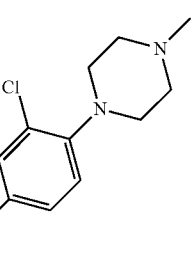
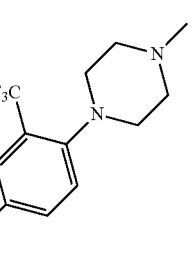
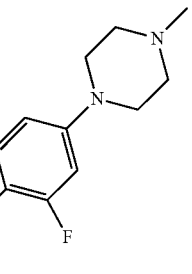

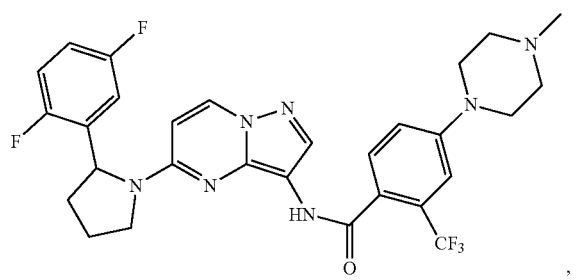,
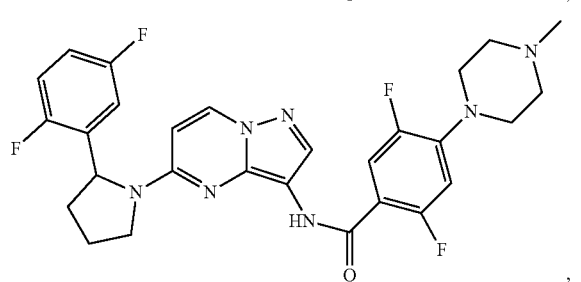,
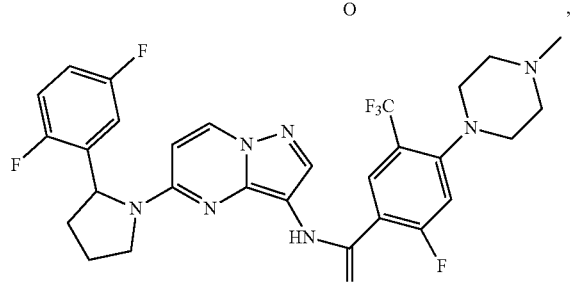,
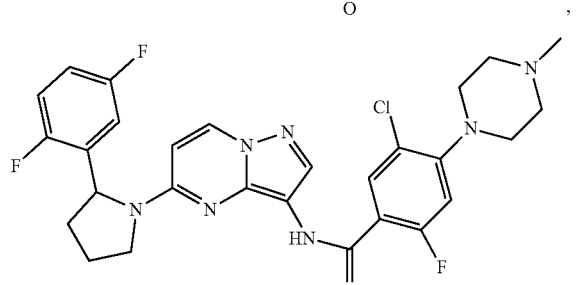,
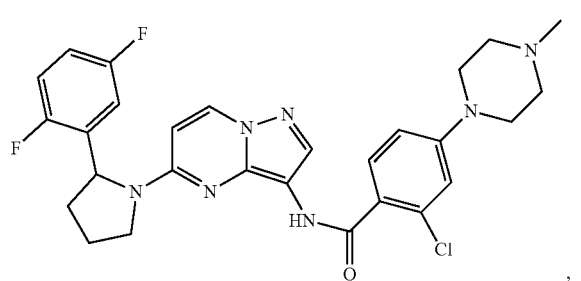,
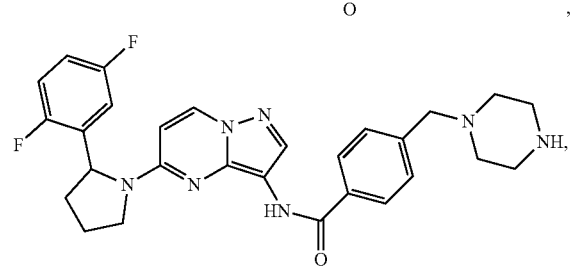,
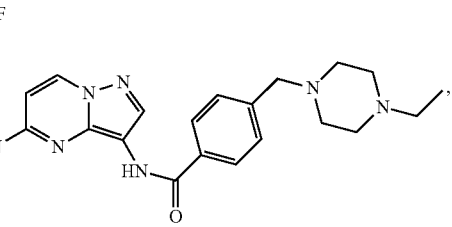,
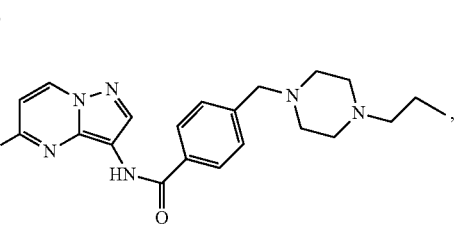,
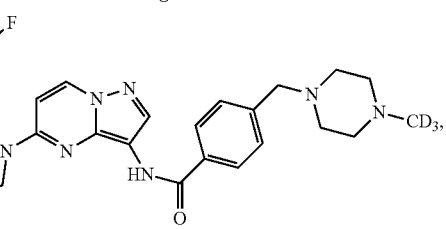,
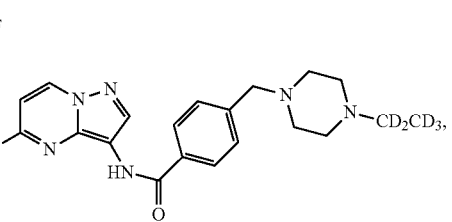,
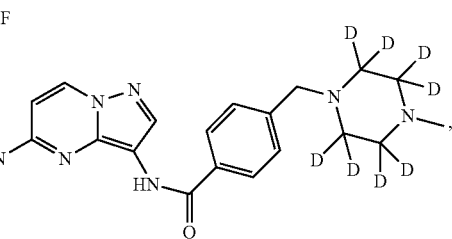,
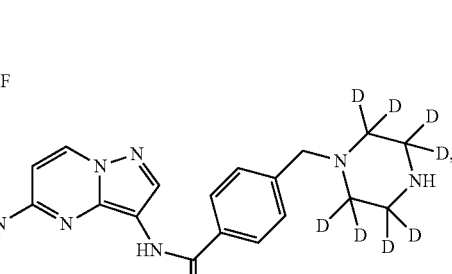,
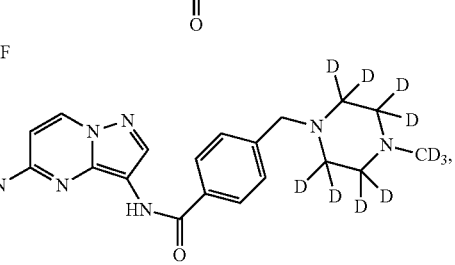,

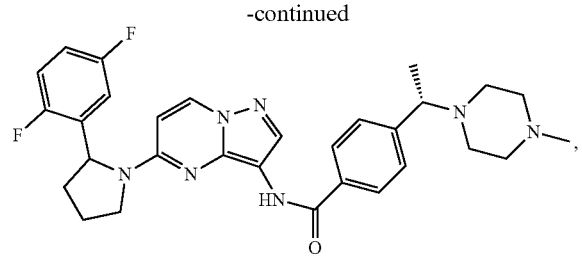
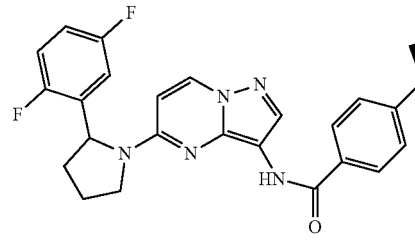
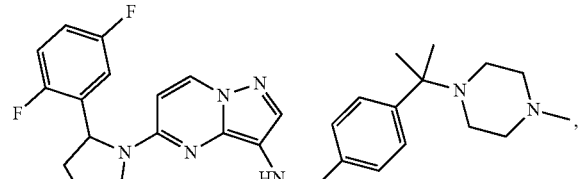
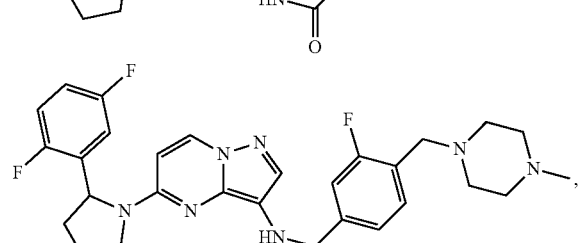
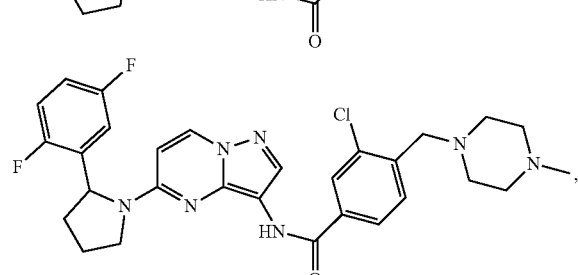
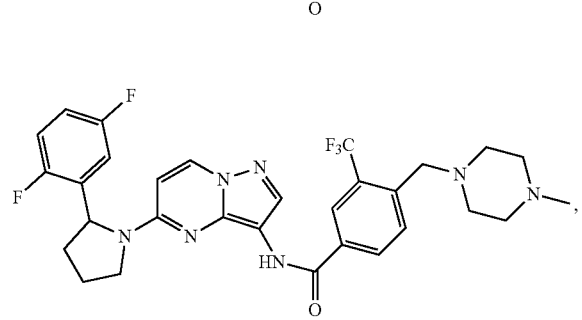
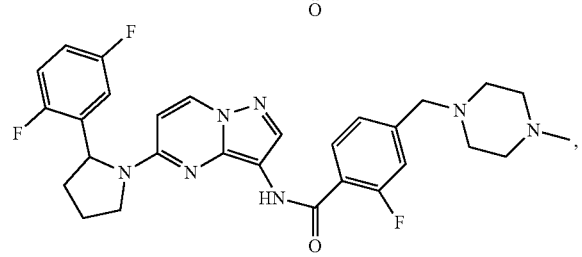
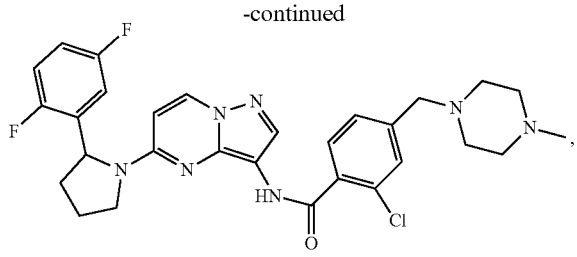
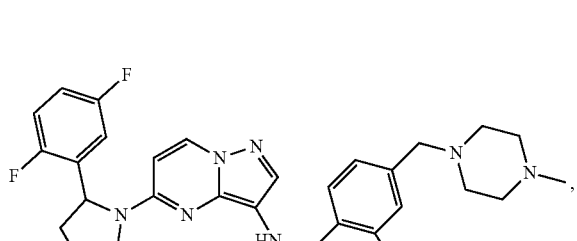
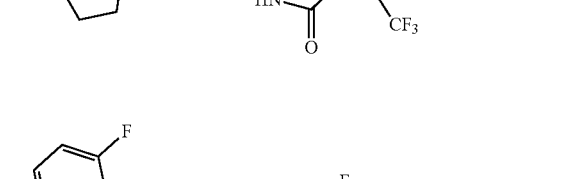
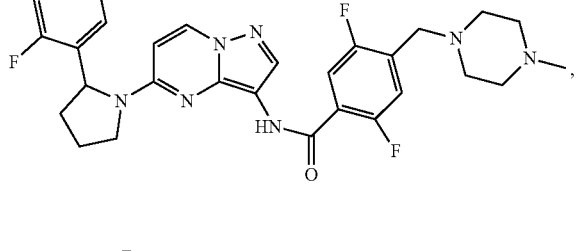
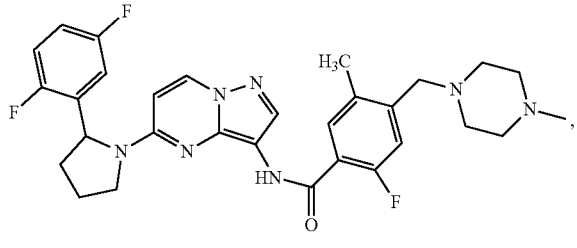
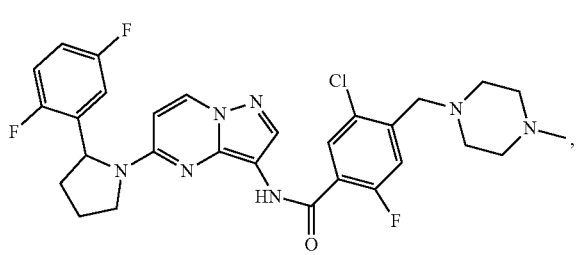
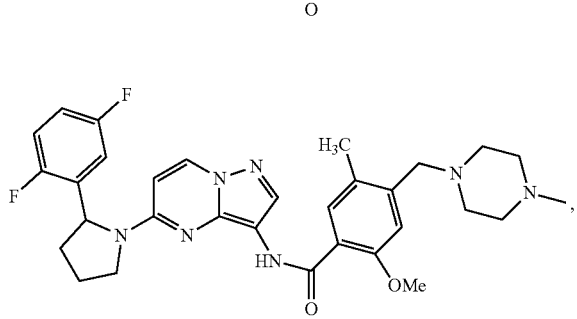

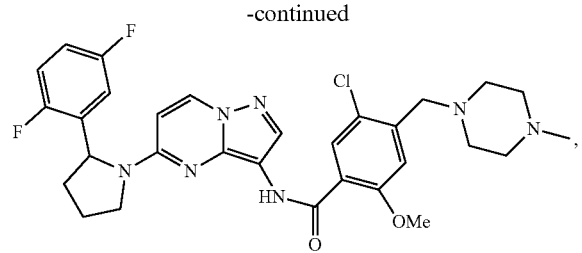
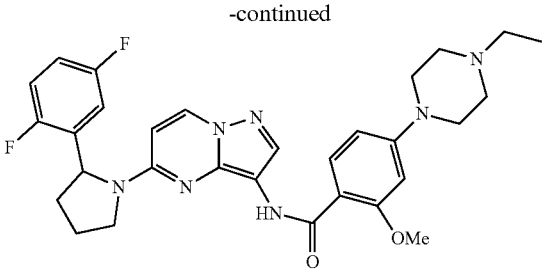
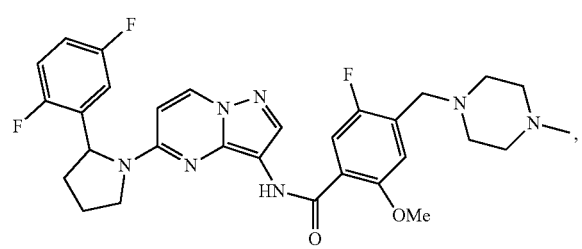
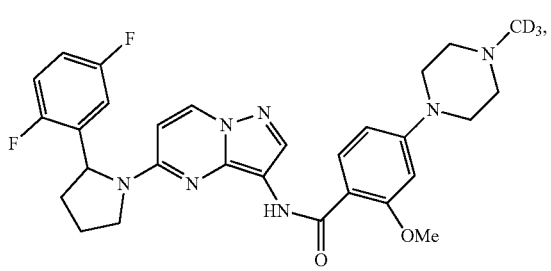
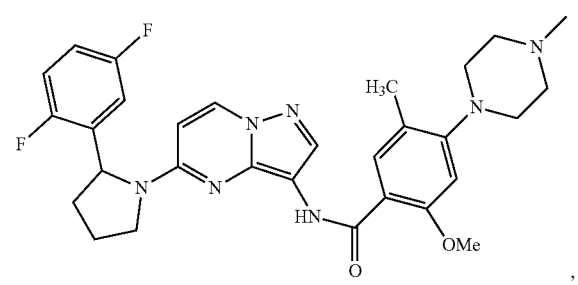
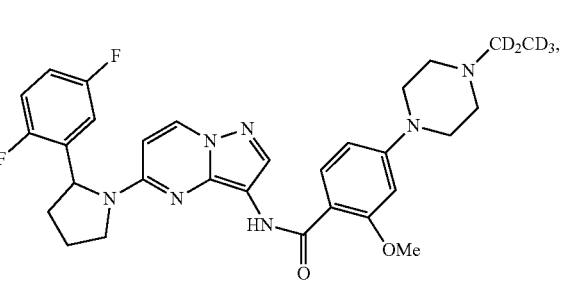
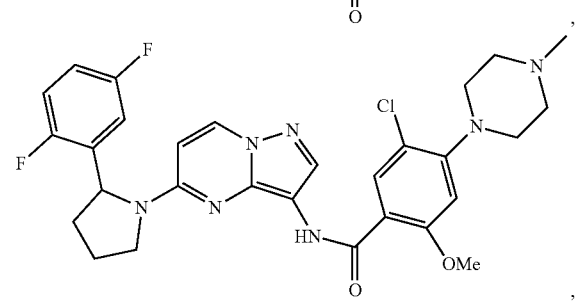
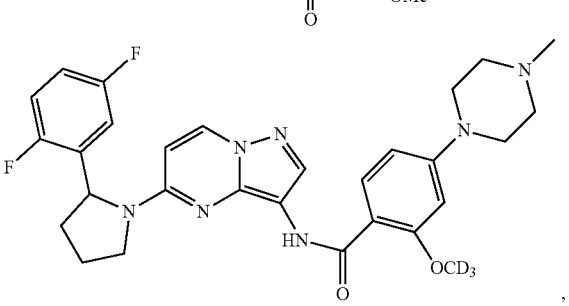
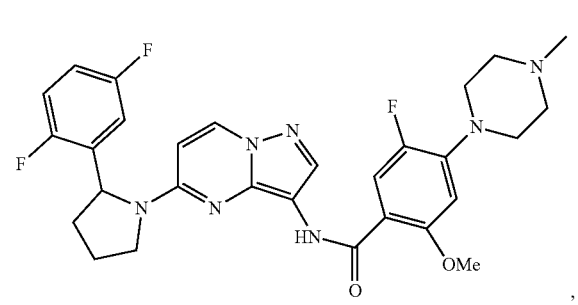
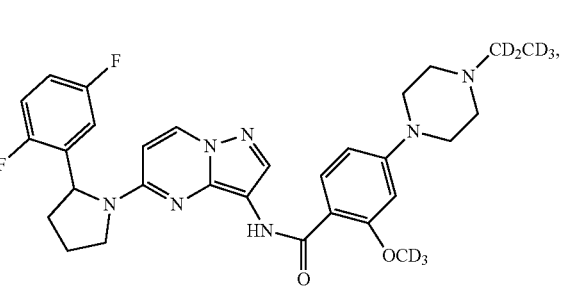
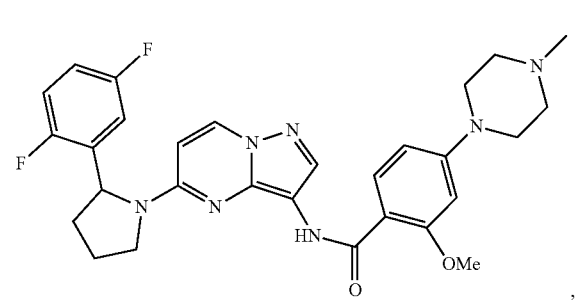
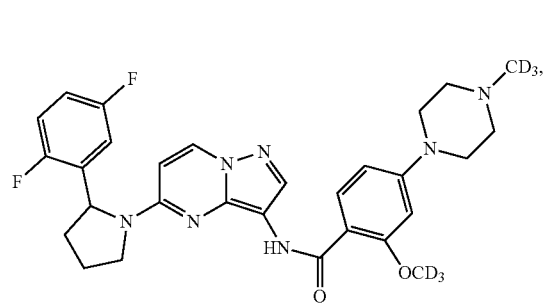

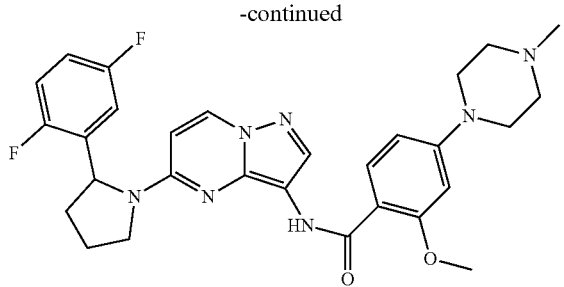,
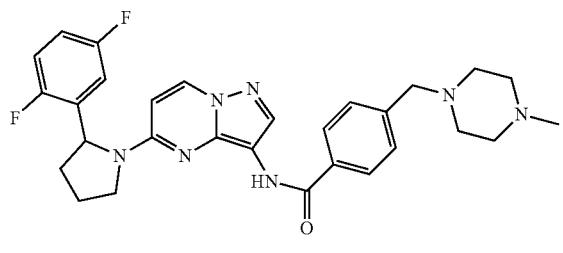 [SMILES: CN1CCN(Cc2ccc(C(=O)Nc3cnn4ccc(N5CCC[C@@H]5c5cc(F)ccc5F)nc34)cc2)CC1],
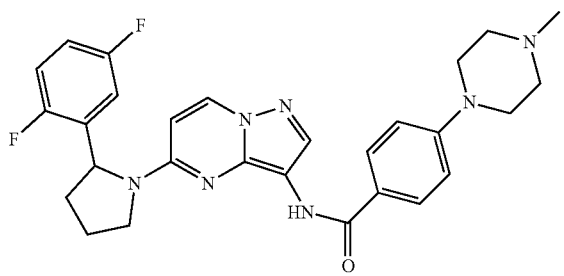,
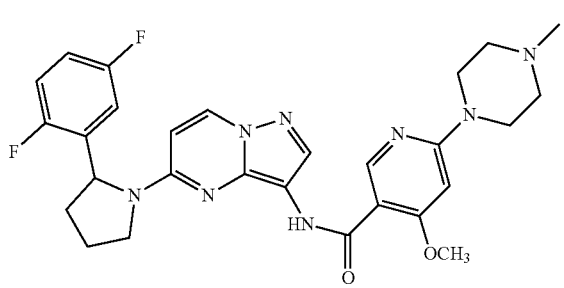,
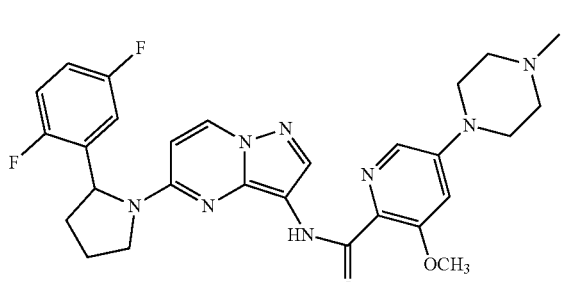,
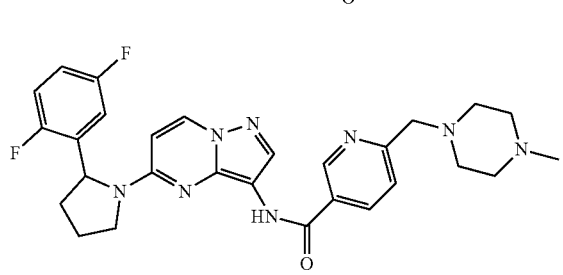,
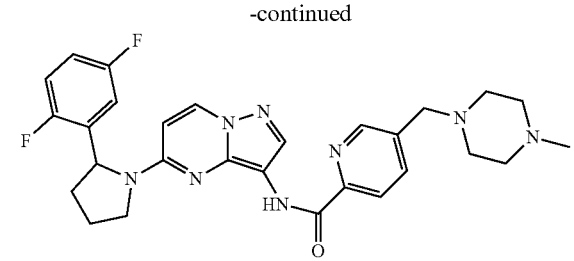,
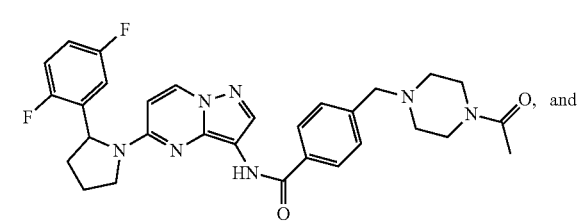, and
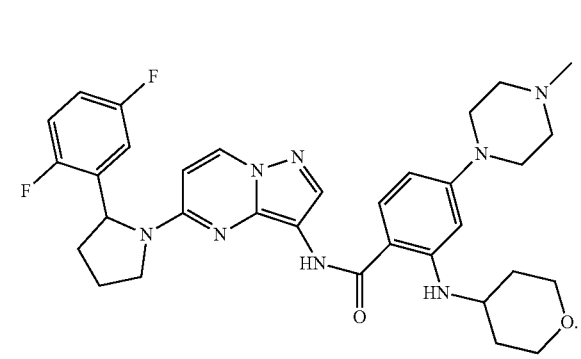.
6. The compound of claim 2, wherein the compound selected from the group consisting of:
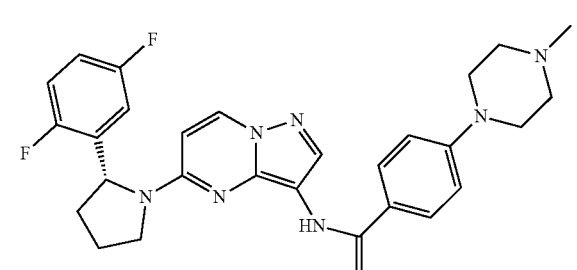,
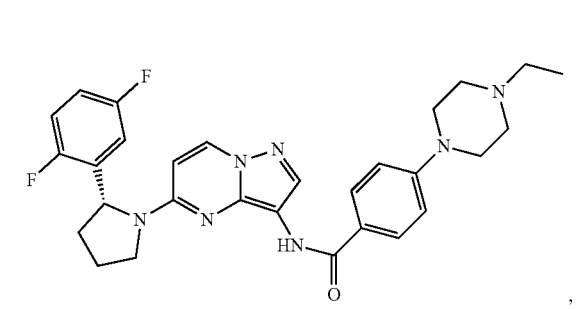, 61
-continued
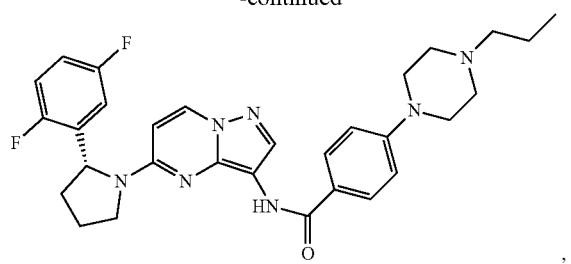
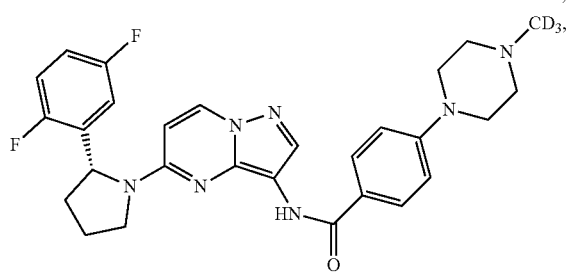
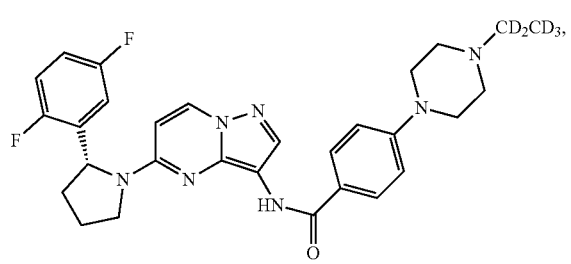
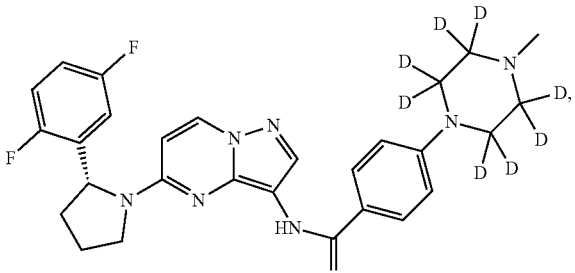
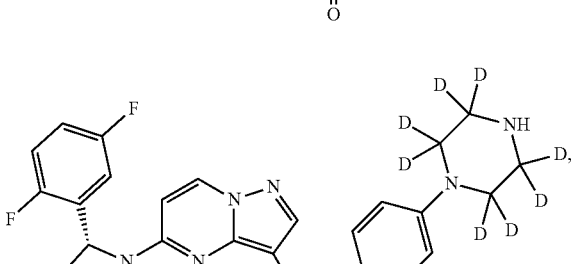
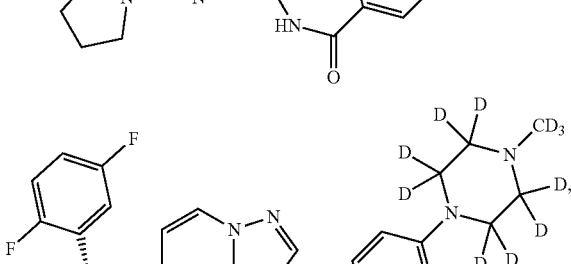
62
-continued
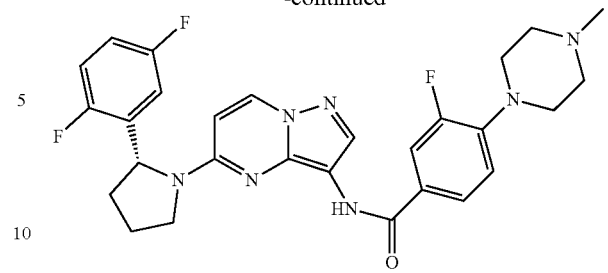
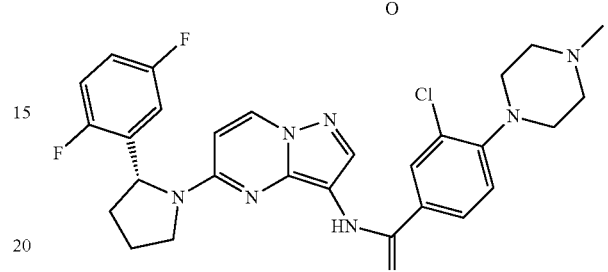
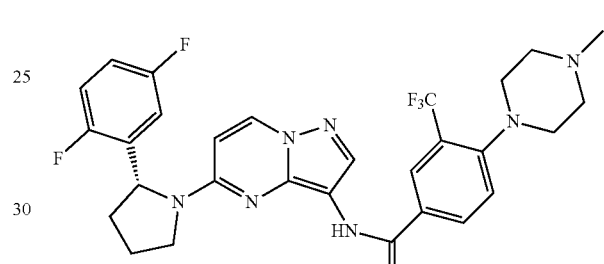
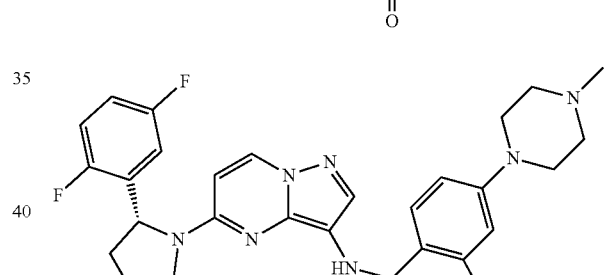
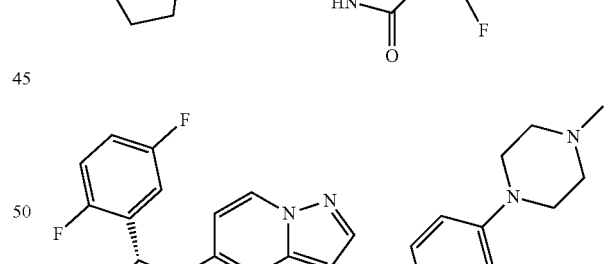
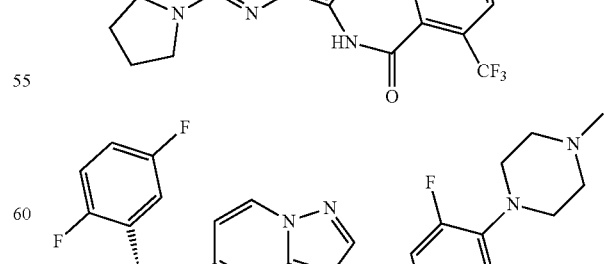

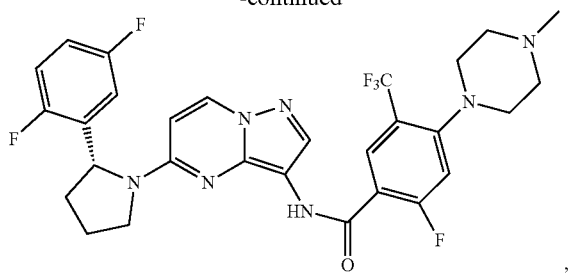
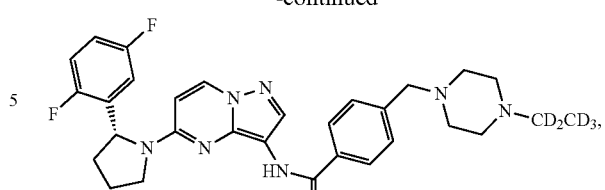
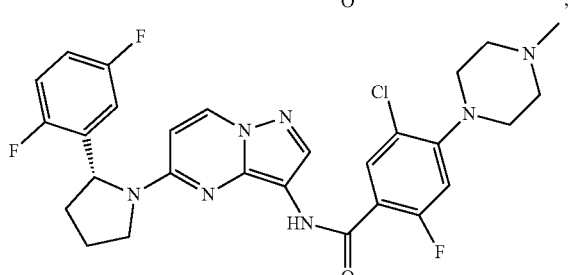
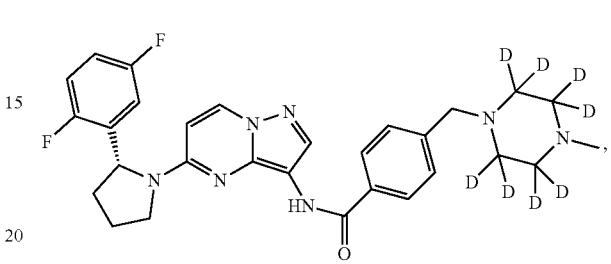
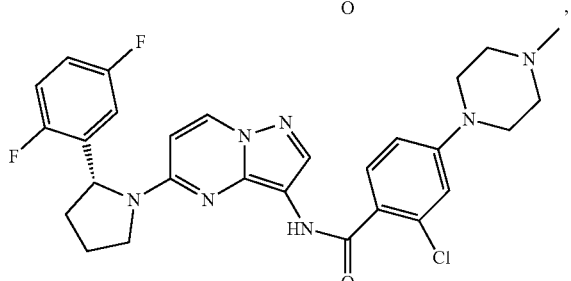
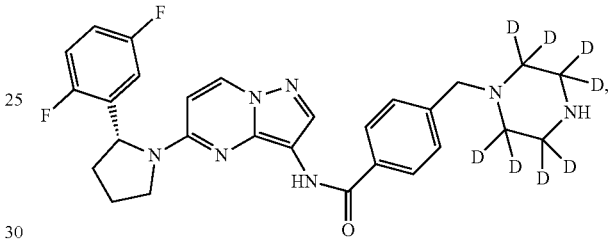
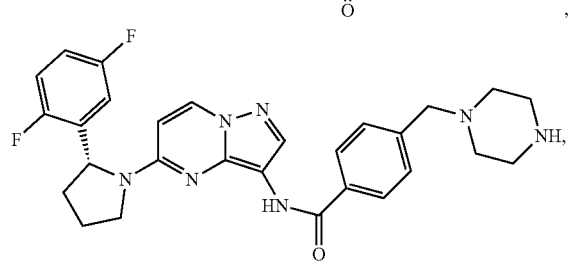
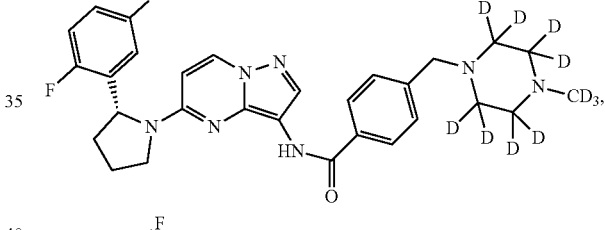
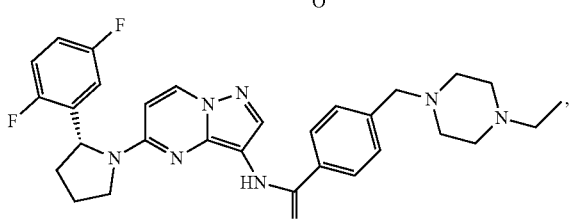
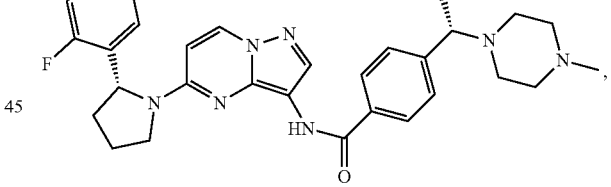
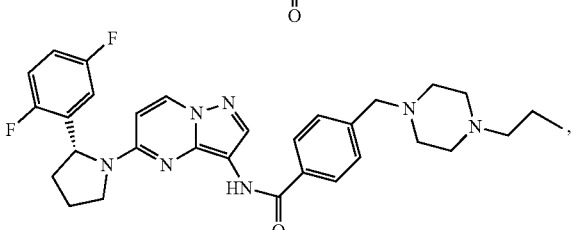
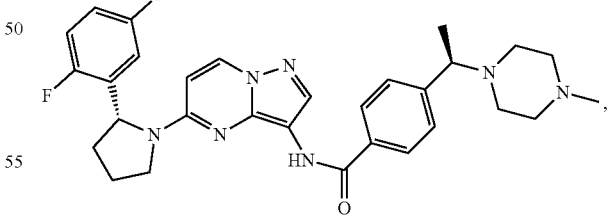
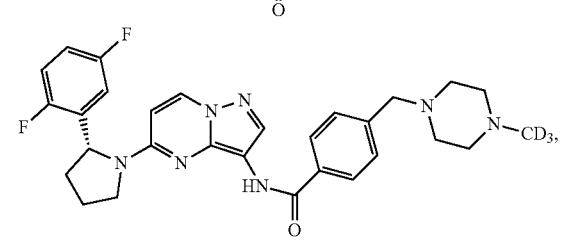
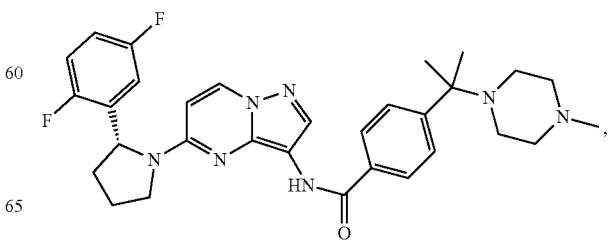

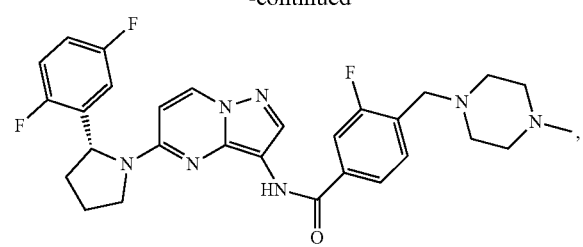
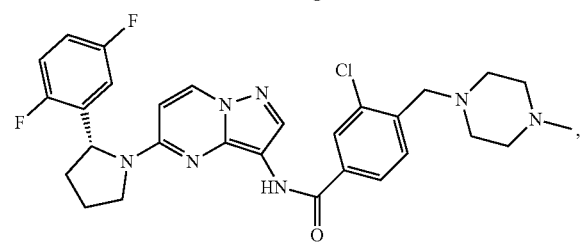
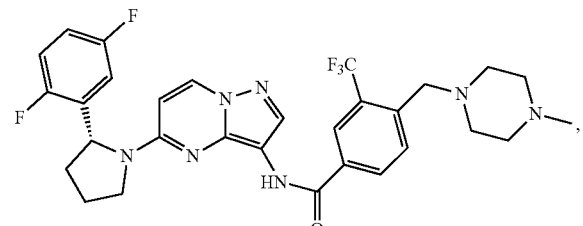
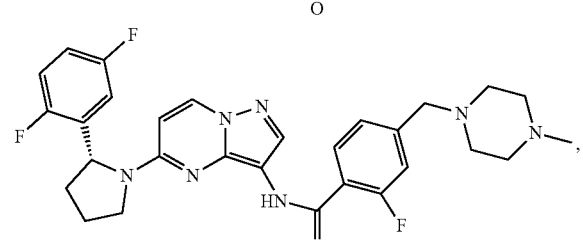
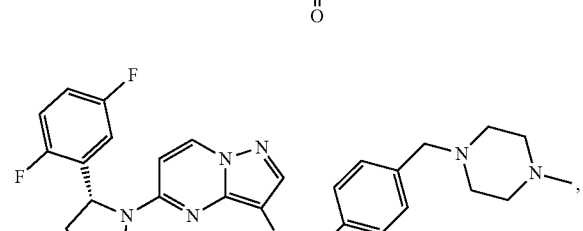
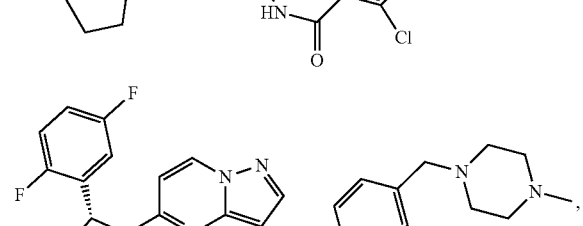
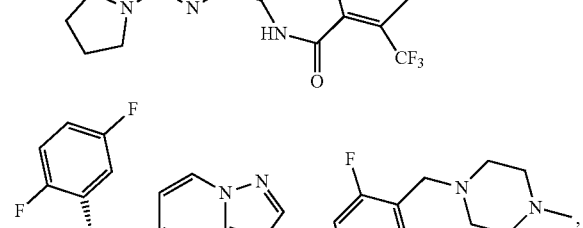
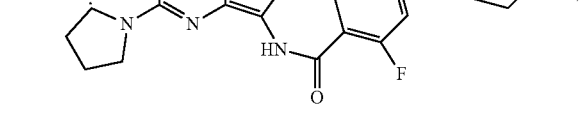
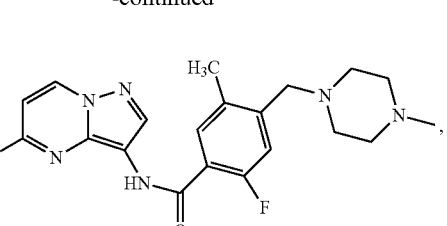
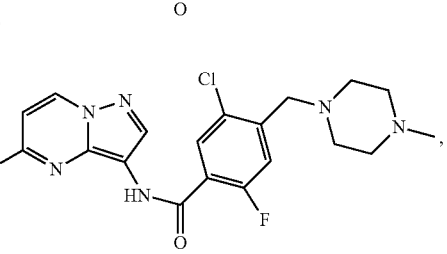
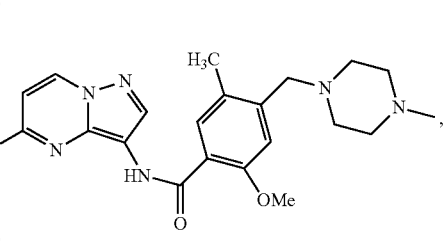
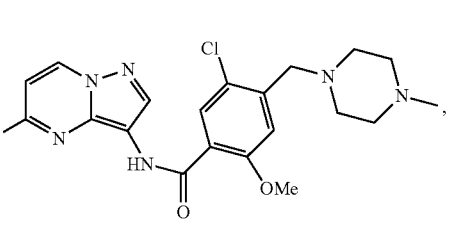
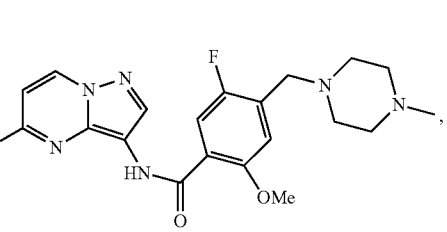
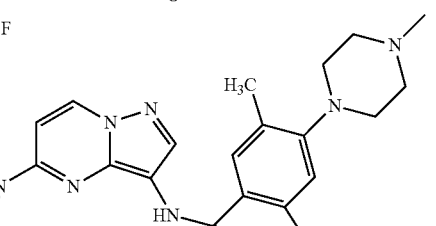
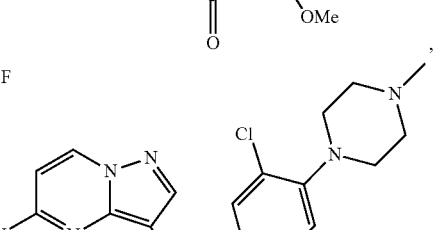
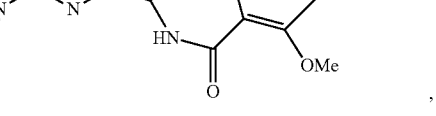

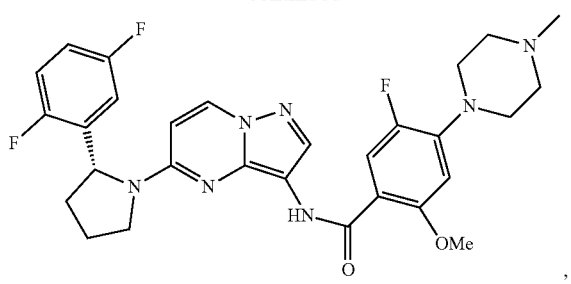,
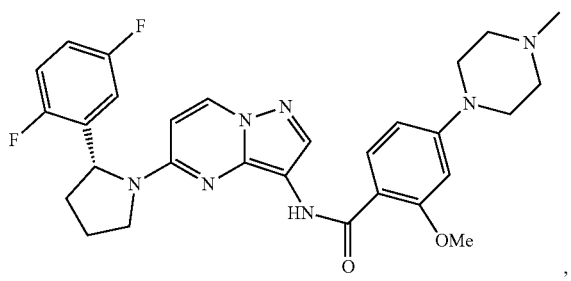,
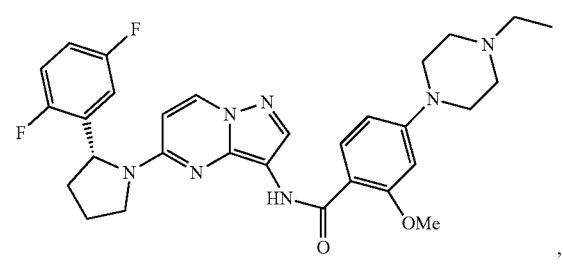,
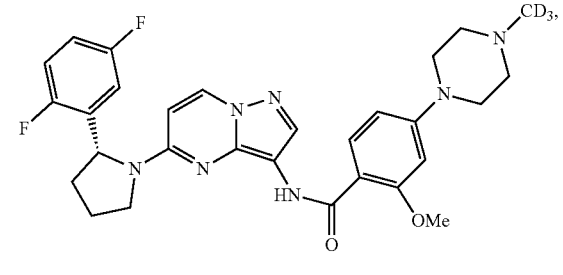,
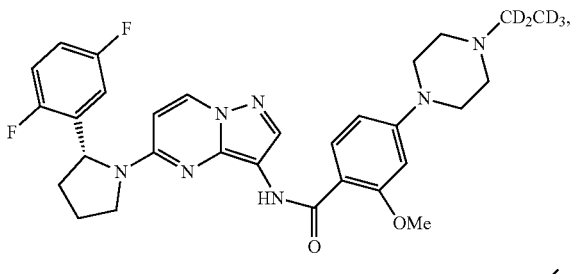,
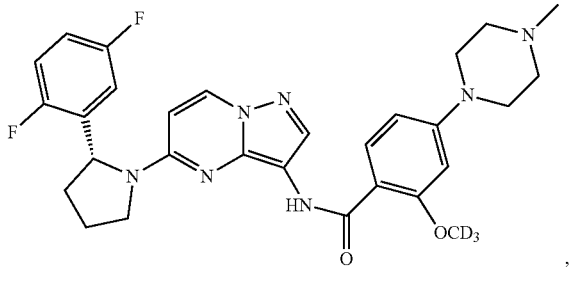,
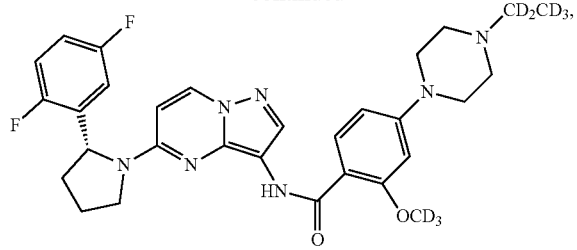,
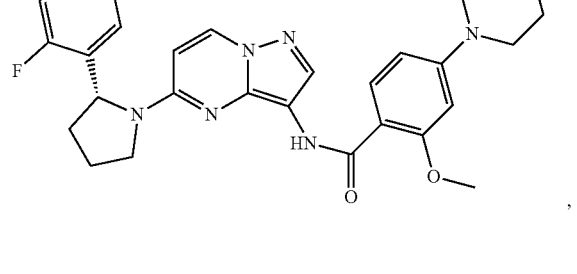,
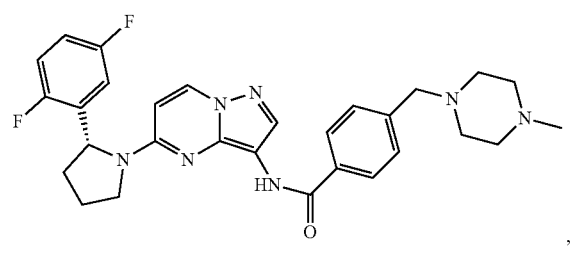,
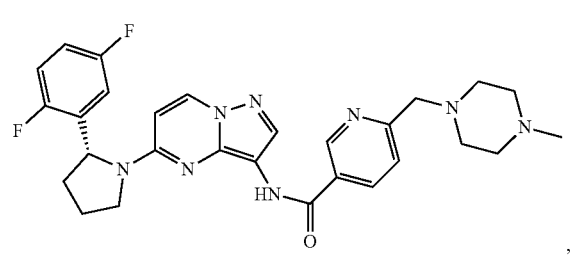,

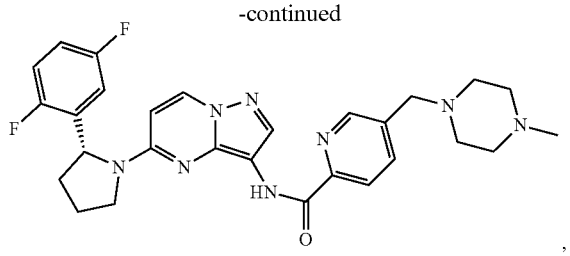

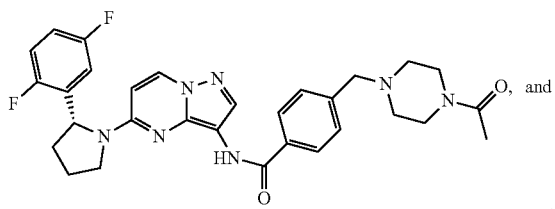

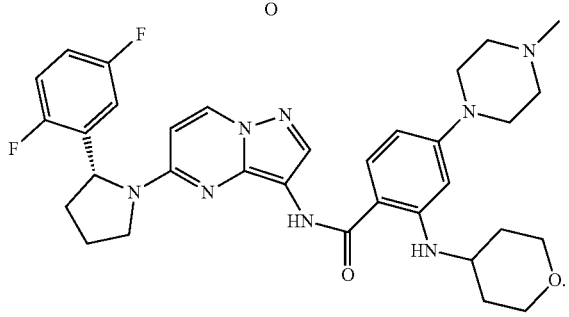

7. A pharmaceutical composition comprising an effective amount of a compound of claim 1, or a pharmaceutically acceptable salt, solvate, stereoisomer, or tautomer thereof, and a pharmaceutically acceptable carrier.

8. A method of inhibition of TrkA in a patient, comprising the step of administering to the patient in need thereof the pharmaceutical composition of claim 7.

9. The compound of claim 1, or a pharmaceutically acceptable salt, solvate, stereoisomer, or tautomer thereof for use as a medicament.

10. The compound of claim 1, or a pharmaceutically acceptable salt, solvate, stereoisomer, or tautomer thereof for use as a medicament for inhibition of TrkA.

11. The compound of claim 1, or a pharmaceutically acceptable salt, solvate, stereoisomer, or tautomer thereof for use in a method of regulating the kinase signaling transduction.

12. A pharmaceutical composition comprising an effective amount of a compound of claim 1, or a pharmaceutically acceptable salt, solvate, stereoisomer, or tautomer thereof, in combination with one or more anti-cancer agents for use in a method of inhibition of TrkA.

13. A compound according to Formula I or II:

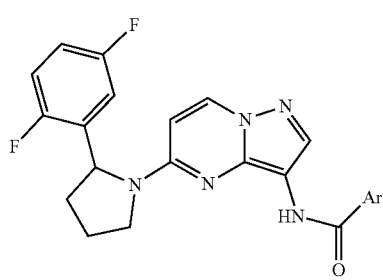

I

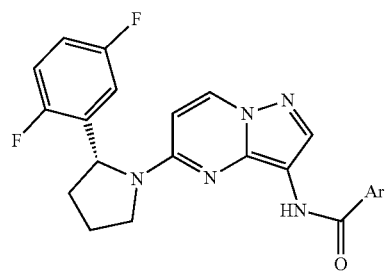

II or a pharmaceutically acceptable salt, solvate, stereoisomer, or tautomer thereof, wherein Ar is:

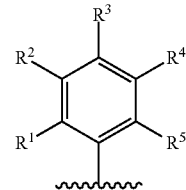

wherein at least one of $R^1$, $R^2$, $R^3$, $R^4$, and $R^5$ is not hydrogen, each of $R^1$, $R^2$, $R^3$, $R^4$, and $R^5$ is independently hydrogen, halide, $C_1$-$C_6$ alkyl, $C_1$-$C_6$alkyloxy, $C_2$-$C_6$alkenyl, $C_2$-$C_6$alkynyl, $C_3$-$C_6$cycloalkyl, $C_6$-$C_{12}$ aryl, 3-12 membered heteroalicyclic, 5-12 membered heteroaryl, $NO_2$, —$NR^6R^7$, —$CR^8R^9(CR^8R^9)_nR^6$, CN, —$C(O)R^6$, —$O(CO)R^6$, —$OCR^8R^9(CR^8R^9)_nNR^6R^7$, —$OCR^8R^9(CR^8R^9)_nOR^6$, —$NR^6C(O)R^7$, —$(CR^8R^9)_nC(O)OR^6$, —$(CR^8R^9)_nC(O)NR^6R^7$, —$CR^8R^9(CR^8R^9)_nNR^6R^7$, —$NR^6(CO)$—$NR^6R^7$, —$S(O)_tR^6$, or —$S(O)_2NR^6R^7$, wherein two groups among $R^1$, $R^2$, $R^3$, $R^4$, and $R^5$ on adjacent atoms of the phenyl may, together with the adjacent atoms to which two groups are bound, be combined to form a $C_6$-$C_{12}$ aryl, 5-12 membered heteroaryl, $C_3$-$C_{12}$ cycloalkyl or 3-12 membered heteroalicyclic, wherein each aryl, heteroalicyclic, and heteroaryl is unsubstituted or independently substituted with one or more hydrogen deuterium or $C_1$-$C_3$ alkyl; with the proviso that the heteroatom of 3-12 membered heteroalicyclic is not attached to the phenyl;

each of $R^6$, $R^7$, $R^8$, and $R^9$ is independently hydrogen, $C_1$-$C_6$ alkyl; $C_6$-$C_{12}$ aryl, 5-12 membered heteroaryl, $C_3$-$C_{12}$ cycloalkyl or 3-12 membered heteroalicyclic; or any two of $R^6$, $R^7$, $R^8$, and $R^9$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from the group consisting of N, O, and S; or any two of $R^6$, $R^7$, $R^8$, and $R^9$ bound to the same carbon atom may, together with the carbon to which they are bound, be combined to form a $C_6$-$C_{12}$ aryl, 5-12 membered heteroaryl, $C_3$-$C_{12}$ cycloalkyl, or 3-12 membered heteroalicyclic group;

each n is independently 0, 1, 2, 3, or 4;
each p is independently 1 or 2; and
each t is independently 0, 1, or 2.

14. The compound of claim 13, wherein Ar is:

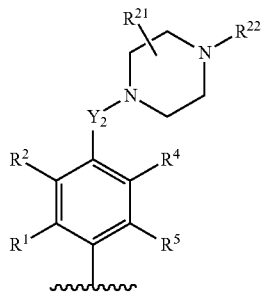

wherein $Y_2$ is a bond or $CR^{23}R^{24}$;

each of $R^1$, $R^2$, $R^4$, and $R^5$ is independently hydrogen, halide, $CF_3$, $C_1$-$C_3$ alkyl, $NO_2$, $C_1$-$C_3$ alkoxyl, or oxan-4-ylamino;

$R^{21}$ is one or more groups independently selected from the group consisting of hydrogen, $C_1$-$C_3$ alkyl and deuterium;

$R^{22}$ is $C_1$-$C_3$ alkyl, or hydrogen; and each of $R^{23}$ and $R^{24}$ is independently hydrogen, deuterium, or $C_1$-$C_3$ alkyl.

15. The compound of claim 2, wherein Ar is:

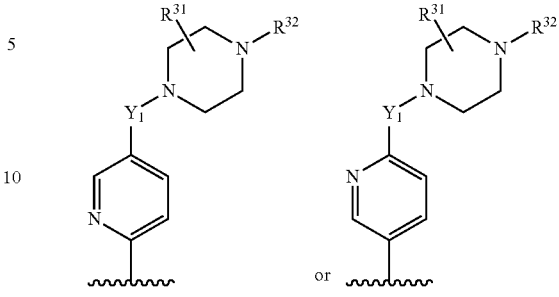

wherein $Y_1$ is a bond or $CR^{23}R^{24}$;

$R^{31}$ is one or more groups independently selected from the group consisting of hydrogen, $C_1$-$C_3$ alkyl and deuterium;

$R^{32}$ is $C_1$-$C_3$ alkyl, $CO(C_1$-$C_3$ alkyl) or hydrogen; and each of $R^{23}$ and $R^{24}$ is independently hydrogen, deuterium, or $C_1$-$C_3$ alkyl.

16. A pharmaceutical composition comprising an effective amount of a compound of claim 2, or a pharmaceutically acceptable salt, solvate, stereoisomer, or tautomer thereof, and a pharmaceutically acceptable carrier.

17. A method of inhibition of TrkA in a patient, comprising the step of administering to the patient in need thereof the pharmaceutical composition of claim 16.

18. A pharmaceutical composition comprising an effective amount of a compound of claim 2, or a pharmaceutically acceptable salt, solvate, stereoisomer, or tautomer thereof, in combination with one or more anti-cancer agents for use in a method of inhibition of TrkA.

* * * * *

```
SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: misc_feature
<223> OTHER INFORMATION: N-term 5-FAM
<220> FEATURE:
<221> NAME/KEY: misc_feature
<223> OTHER INFORMATION: C-term NH2

<400> SEQUENCE: 1

Glu Glu Pro Leu Tyr Trp Ser Phe Pro Ala Lys Lys Lys
1               5                   10
```